US009057702B2

(12) United States Patent
Ozcan et al.

(10) Patent No.: US 9,057,702 B2
(45) Date of Patent: Jun. 16, 2015

(54) COMPACT WIDE-FIELD FLUORESCENT IMAGING ON A MOBILE DEVICE

(71) Applicant: THE REGENTS OF THE UNIVERSITY OF CALIFORNIA, Oakland, CA (US)

(72) Inventors: Aydogan Ozcan, Los Angeles, CA (US); Hongying Zhu, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 13 days.

(21) Appl. No.: 13/769,043

(22) Filed: Feb. 15, 2013

(65) Prior Publication Data

US 2013/0157351 A1    Jun. 20, 2013

Related U.S. Application Data

(63) Continuation-in-part of application No. 13/333,861, filed on Dec. 21, 2011.

(60) Provisional application No. 61/425,665, filed on Dec. 21, 2010, provisional application No. 61/509,985, filed on Jul. 20, 2011, provisional application No. 61/600,534, filed on Feb. 17, 2012.

(51) Int. Cl.
    *G01N 21/64* (2006.01)
    *G01N 21/00* (2006.01)
    (Continued)

(52) U.S. Cl.
    CPC .......... *G01N 21/6486* (2013.01); *G02B 23/243* (2013.01); *G02B 7/006* (2013.01);
    (Continued)

(58) Field of Classification Search
    None
    See application file for complete search history.

(56) References Cited

U.S. PATENT DOCUMENTS 5,104,512 A * 4/1992 Gombocz et al. ............. 204/607
5,439,578 A * 8/1995 Dovichi et al. ............... 204/603
(Continued)

FOREIGN PATENT DOCUMENTS

| KR | 10-0513156 B1 | 8/2005 |
| WO | WO 2006/083081 A1 | 8/2006 |
| WO | WO 2009/088930 A2 | 7/2009 |

OTHER PUBLICATIONS

PCT International Preliminary Report on Patentability (Chapter I of the Patent Cooperation Treaty) for PCT/US2011/066647, Applicant: The Regents of the University of California, Form PCT/IB/326 and 373, dated Jul. 4, 2013 (8pages).
(Continued)

*Primary Examiner* — Neil N Turk
(74) *Attorney, Agent, or Firm* — Vista IP Law Group LLP

(57) ABSTRACT

Wide-field fluorescent imaging on a mobile device having a camera is accomplished with a compact, light-weight and inexpensive optical components that are mechanically secured to the mobile device in a removable housing. Battery powered light-emitting diodes (LEDs) contained in the housing pump the sample of interest from the side using butt-coupling, where the pump light is guided within the sample holder to uniformly excite the specimen. The fluorescent emission from the sample is then imaged using an additional lens that is positioned adjacent to the existing lens of the mobile device. A color filter is sufficient to create the dark-field background required for fluorescent imaging, without the need for expensive thin-film interference filters.

13 Claims, 17 Drawing Sheets

(51) Int. Cl.
| | |
|---|---|
| *G02B 23/24* | (2006.01) |
| *G02B 7/00* | (2006.01) |
| *G02B 7/02* | (2006.01) |
| *G02B 13/00* | (2006.01) |
| *H04M 1/02* | (2006.01) |
| *H04N 5/225* | (2006.01) |
| *G01N 21/76* | (2006.01) |
| *H04M 1/21* | (2006.01) |

(52) U.S. Cl.
CPC .............. *G02B 7/02* (2013.01); *G02B 13/0025* (2013.01); *G01N 21/6458* (2013.01); *H04M 1/0254* (2013.01); *H04M 1/21* (2013.01); *H04N 5/2254* (2013.01); *G01N 2201/0221* (2013.01); *H04M 2250/52* (2013.01)

(56) References Cited

U.S. PATENT DOCUMENTS

| | | | |
|---|---|---|---|
| 2003/0112432 A1 | 6/2003 | Yguerabide et al. | |
| 2003/0160182 A1* | 8/2003 | Petrich et al. | 250/458.1 |
| 2005/0023155 A1* | 2/2005 | Sawyer et al. | 205/792 |
| 2005/0030534 A1* | 2/2005 | Oldham et al. | 356/344 |
| 2006/0222567 A1 | 10/2006 | Kloepfer et al. | |
| 2007/0098600 A1* | 5/2007 | Kayyem | 422/102 |

OTHER PUBLICATIONS

Candes, E.J. et al., Stable Signal Recovery from Incomplete and Inaccurate Measurements, Comm. Pure Appl. Math., 2006, 59, 1207-1223.

Candes, E.J. et al., Near Optimal Signal Recovery From Random Projections: Universal Encoding Strategies?, IEEE Trans. Inform. Theory, 2006, 52, 5406-5425.

Donoho, D.L., Compressed Sensing, IEEE Trans. Inform. Theory, 2006, 52, 1289-1306.

Su, T. et al. Multi-angle lensless digital holography for depth resolved imaging on a chip, Opt. Express, 2010, 18, 9690-9711.

McDonald, J.C. et al., Poly(dimethylsiloxane) as a Material for Fabricating Microfluidic Devices, Acc. Chem. Res., 2001, 35, 491-499.

Suzuki, S et al., Topological Structural Analysis of Digitized Binary Images by Border Following, Comput. Vis. Graph. Image Process., 1985, 30, 32-46.

Breslauer, David N. et al., Mobile Phone Based Clinical Microscopy for Global Health Applications, PLoS ONE, www.plosone.org, Jul. 2009, vol. 4, Issue 7, e6320.

Zhu, Hongying et al., Cost-effective and compact wide-field fluorescent imaging on a cell-phone, Lab on a Chip, Epub. Nov. 9, 2010, vol. 11, No. 2, pp. 315-322.

Zhu, Hongying et al., Optofluidic Fluorescent Imaging Cytometry on a Cell Phone, Anal Chem. Sep. 1, 2011, Epub. Aug. 2, 2011, vol. 83, No. 17, pp. 6641-6664.

PCT International Search Report for PCT/US2011/066647, Applicant: The Regents of the University of California, Form PCT/ISA/210 and 220, dated Sep. 12, 2012 (4pages).

PCT Written Opinion of the International Search Authority for PCT/US2011/066647, Applicant: The Regents of the University of California, Form PCT/ISA/237, dated Sep. 12, 2012 (6pages).

Hardie et al., Joint MAP Registration and High-Resolution Image Estimation Using a Sequence of Undersampled Images, IEEE, vol. 6 No. 12, Dec. 1997.

Ozcan et al., Ultra wide-filed lens-free monitoring of cells on-chip, Lab on Chip 8, 89-106, Nov. 1, 2007.

Ozcan et al., Lens-free On-Chip Cytometry for wireless Health Diagnosis, IEEE LEOS Newsletter, Oct. 2008.

Seo et al., Lensfree On-chip Cytometry Using Tunable Monochromatic Illumination and Digital Noise Reduction, Multi-color LUCAS, Sep. 2008.

Seo et al., Lensfree holographic imaging for on-chip cytometry and diagnostics, Lab on a Chip, 9, 777-787, Dec. 5, 2008.

Su et al., Towards Wireless Health: Lensless On-Chip Cytometry, Biophotonics, Dec. 2008.

Su et al., High-Throughput Lensfree Imaging and Characterization of Heterogeneous Cell Solution on a Chip, Biotechnology and Bioengineering, Sep. 8, 2008.

Isikman et al., Lensfree Cell Holography on a Chip: From Holographic Cell Signatures to Microscopic Reconstruction, LEOS Annual Meeting Conf. Proceedings, Oct. 2009.

Mudanyali et al., Lensless On-chip Imaging of Cells Provides a New Tool for High-throughput Cell-Biology and Medical Diagostics, Journal of Visualized Experiments, Dec. 14, 2009.

Bishara et al., Lensfree on-chip microscopy over a wide field-of-view using pixel super-resolution, Optics Express, vol. 18 No. 11, May 24, 2010.

Coskun et al., Wide field-of-view lens-free fluorescent imaging on a chip, Lab Chip, 10(7), 824-827, Apr. 7, 2010.

Coskun et al., Lensless wide-field fluorescent imaging on a chip using compressive decoding of sparse objects, Optics Express, vol. 18 No. 10, May 5, 2010.

Khademhosseinieh et al., Lensfree color imaging on a nanostructured chip using compressive decoding, Applied Physics Letters, 97, 211112-1, Nov. 24, 2010.

Khademhosseinieh et al., Lensfree on-chip imaging using nanostructured surfaces, Applied Physics Letters, 96, 171106, Apr. 30, 2010.

Mudanyali et al., Compact, light-weight and cost-effective microscope based on lensless incoherent holography for telemedicine applications, Lab Chip, 10, 1417-1428, Apr. 19, 2010.

Ozcan, Smart technology for global access to healthcare, SPIE, Mar. 16, 2010.

Ozcan et al., Lensfree on-chip holography facilitates novel microscopy applications, SPIE, May 19, 2010.

File History of U.S. Appl. No. 13/333,861, filed Dec. 21, 2011, Inventor: Aydogan Ozcan et al. including an Office Action dated Jun. 2, 2014, (26pages).

\* cited by examiner

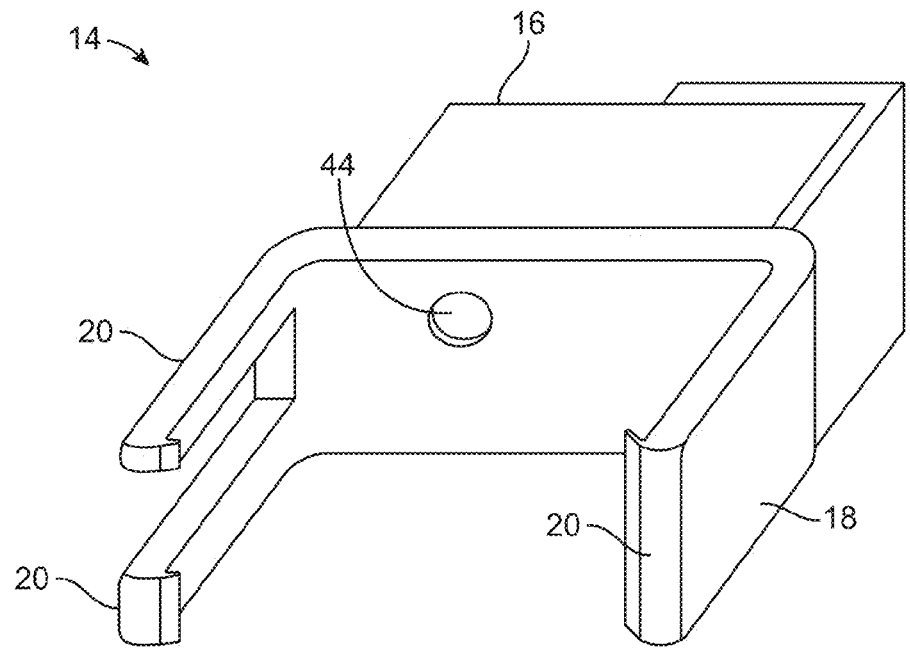
FIG. 1A
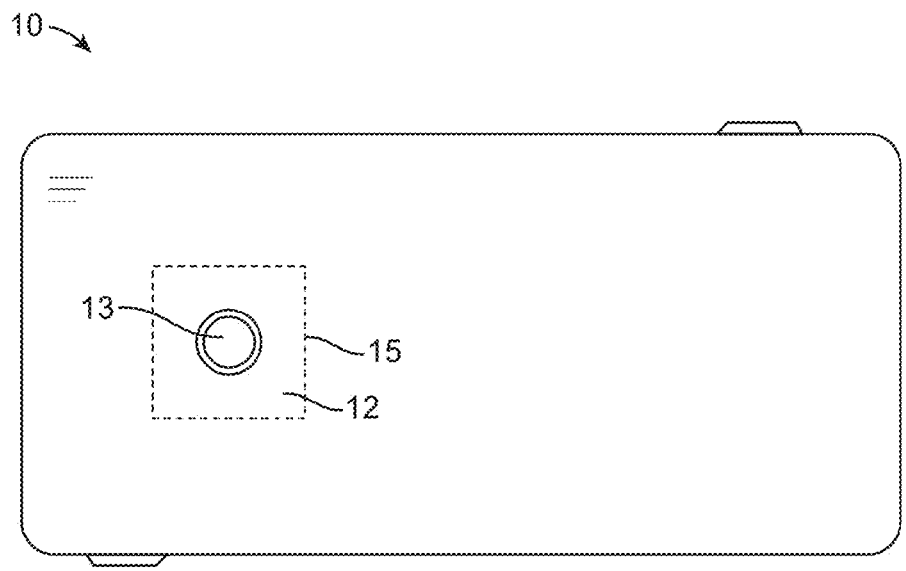

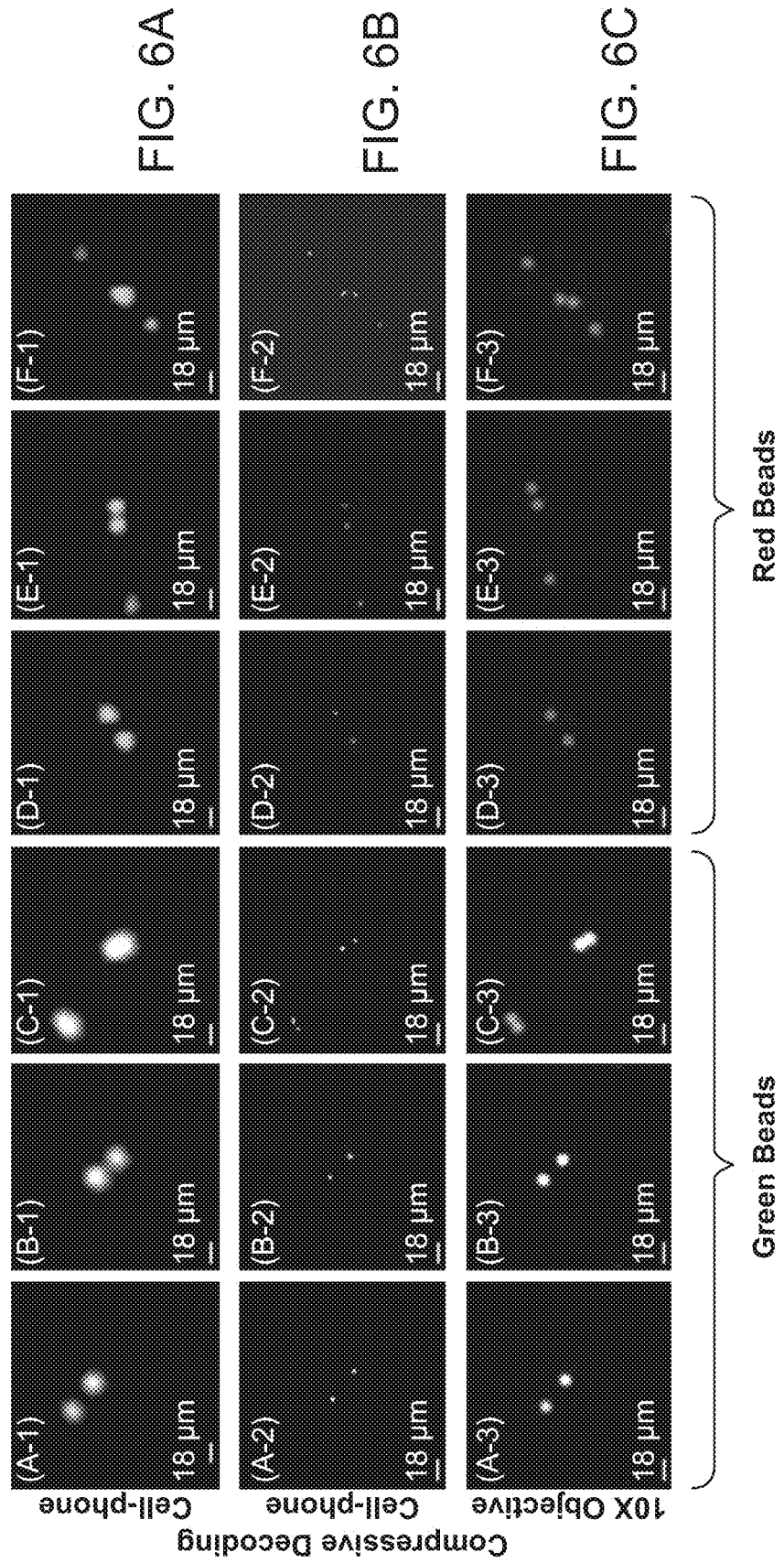

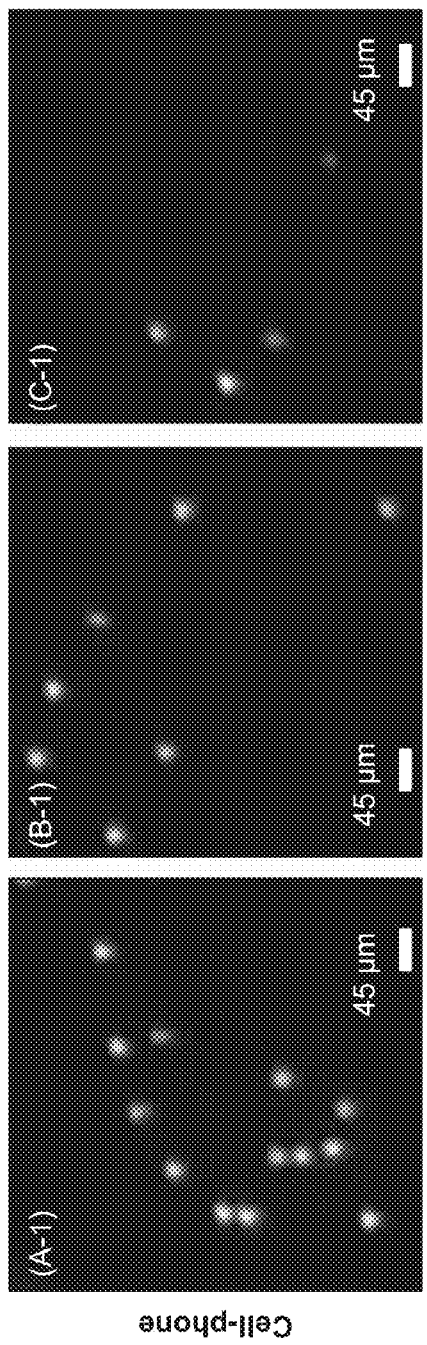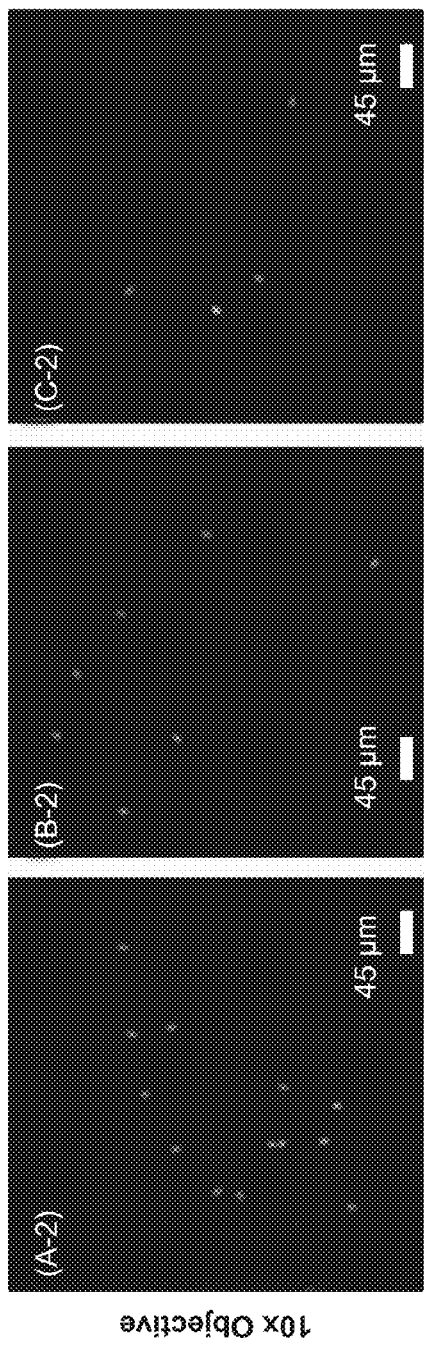
FIG. 8A
FIG. 8B

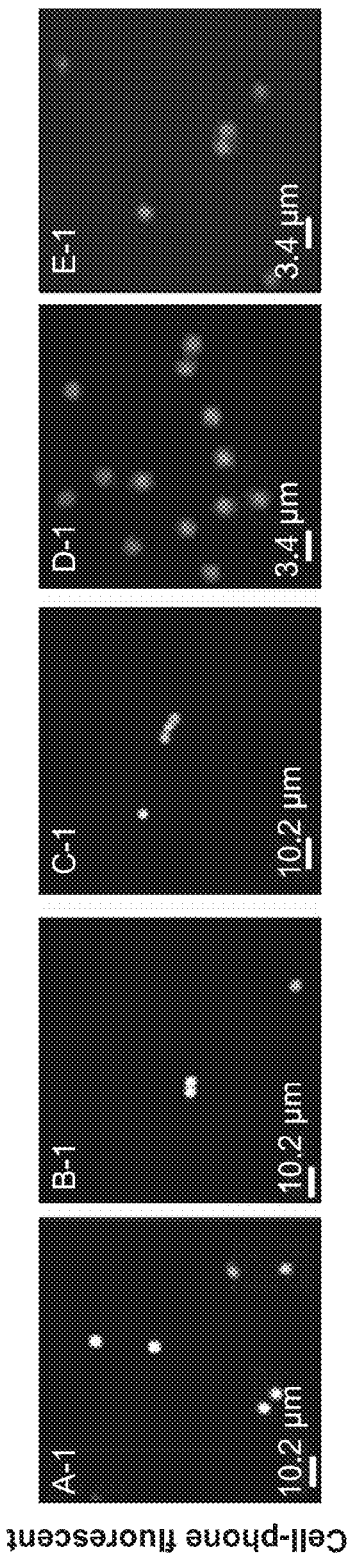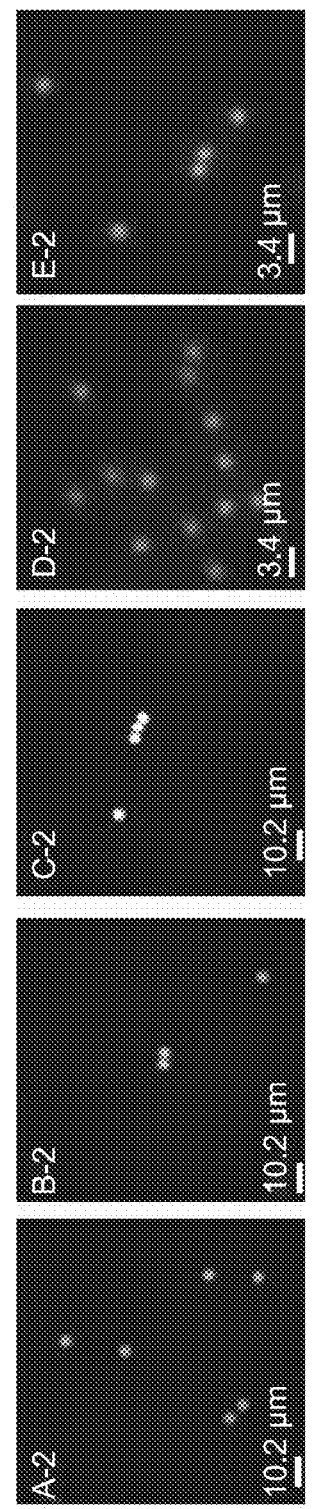
FIG. 12A
FIG. 12B

COMPACT WIDE-FIELD FLUORESCENT IMAGING ON A MOBILE DEVICE

RELATED APPLICATIONS

This Application is a continuation-in-part of and claims priority to U.S. patent application Ser. No. 13/333,861 filed on Dec. 21, 2011, which itself claims priority to U.S. Provisional Patent Application No. 61/425,665 filed on Dec. 21, 2010 and U.S. Provisional Patent Application No. 61/509,985 filed on Jul. 20, 2011. This application also claims priority to U.S. Provisional Patent Application No. 61/600,534 filed on Feb. 17, 2012. Priority is claimed pursuant to 35 U.S.C. §§119 and 120. The above-noted patent applications are incorporated by reference as if set forth fully herein.

STATEMENT REGARDING FEDERALLY SPONSORED RESEARCH OR DEVELOPMENT

This invention was made with Government support under OD006427, awarded by the National Institutes of Health; 0754880, awarded by the National Science Foundation; and N00014-09-1-0858, awarded by the U.S. Navy, Office of Naval Research. The Government has certain rights in the invention.

FIELD OF THE INVENTION

The field of the invention generally relates to methods and devices for imaging of microscopic structures such as cells and particles. More particularly, the field of the invention pertains to systems and methods for the imaging of cells or particles in a static sample or flowing within a microfluidic environment.

BACKGROUND

Close to 60% of the world population has at least one mobile telephone subscription, a number which is expected to further increase up to ~90% by the year 2015. About two-thirds of these mobile phones are actually being used in the developing world, which holds significant promise for various telemedicine applications potentially impacting the fight against several global health problems. The use of the existing or built-in hardware and/or software architecture contained in mobile phones to improve healthcare is a recently emerging theme, which has already enabled implementation of various telemedicine technologies on mobile devices including electrical impedance tomography, electrocardiography, fluorescent microscopy, and lens-free on-chip microscopy.

Among these technologies, fluorescent microscopy is particularly important since fluorescent markers have gone through a significant advancement over the last decade bringing specificity and sensitivity to various lab-on-a-chip applications including, for example, diagnosis of disease, quantification of target cells/bacteria, or detection of biomarkers. Breslauer et al. has recently demonstrated fluorescent microscopy on a mobile phone that achieves ~1.2 µm resolution across a field-of-view (FOV) of ~0.025 mm$^2$ using a rather large and bulky opto-mechanical attachment that is more than 15 cm in length. See Breslauer D N et al., Mobile Phone Based Clinical Microscopy for Global Health Applications, PLoS ONE 4(7) (2009). The device described in Breslauer et al. uses an LED light source together with conventional optics components including microscope objectives, eyepiece, emission and excitation filters that are positioned in-line which results in the long length of the device. There is still a need for higher throughput platforms that can image much larger sample areas and volumes using more compact and lighter weight telemedicine interfaces. Moreover, prior efforts such as that disclosed in Breslauer et al. generate images of static volumes. There is a need for translating flow-based fluorescent cytometry concepts into small mobile devices. A small imaging flow cytometry device could extend micro-analysis capabilities in resource limited settings to such applications as, for example, conducting whole blood analysis or screening of water-borne parasites in drinking water.

SUMMARY

A mobile device having wide-field fluorescent imaging capability is disclosed. The mobile device, which in a preferred embodiment includes a conventional mobile phone, webcam, or personal digital assistant (PDA) or the like with imaging functionality. The fluorescent imaging system is compact, light-weight and contains relative inexpensive optical components that are mechanically attached (or detached as the case may be) to an existing mobile device.

For example, a separate housing is provided that contains the illumination source, sample holder, power source, filter, and optical elements. In one embodiment, battery powered light-emitting diodes (LEDs) are used to pump the sample of interest from a side location using butt-coupling, where the pumped light was guided within a sample cuvette to uniformly excite the specimen. The fluorescent emission from the sample was then imaged using an additional lens contained in the housing that was positioned in front of the existing lens of the camera contained in the mobile device (e.g., mobile phone). Because the excitation occurs through guided waves that propagate generally perpendicular to the detection path, an inexpensive plastic color filter was sufficient to create the dark-field background required for fluorescent imaging, without the need for expensive thin-film interference filters.

Performance of this platform was confirmed by imaging various fluorescent micro-objects in two (2) colors (i.e., red and green) over a field-of-view (FOV) of ~81 mm$^2$ with a raw spatial resolution of ~20 µm. Additional digital processing of the captured images through the use of compressive sampling theory, an approximately two-fold improvement is achieved in the resolving power without a trade-off in the imaging FOV. The capability of imaging a large FOV would be exceedingly important to probe large sample volumes (e.g., >0.1 mL) of e.g., blood, urine, sputum or water. In this regard, the platform has also been tested to demonstrate fluorescent imaging of labeled white-blood cells from whole blood samples, as well as water-borne pathogenic protozoan parasites such as *Giardia Lamblia* cysts.

Weighing only ~28 grams (~1 ounce), this compact and cost-effective fluorescent imaging platform is modular and may be secured to (and removed when needed) to a variety of different mobile devices having imaging functionality. For example, the platform may be removably secured to a mobile phone and would be quite useful especially for resource-limited settings, and would provide an important tool for wide-field imaging and quantification of various lab-on-a-chip assays developed for global health applications. For instance, the platform may be used for the cost-effective monitoring of HIV+ patients for CD4 counts or viral load measurements.

In one embodiment, a fluorescent imager for use with a mobile device having a camera element includes a housing configured for securement to the mobile device; an array of capillary tubes disposed in the housing containing fluorescently labeled particles and configured to hold a sample; an excitation light source disposed in the housing an oriented to side illuminate the array of capillary tubes; a filter holder disposed in the housing and configured to hold filter media therein; and a lens disposed in the housing, wherein the housing is configured to attach to the mobile device to place the lens adjacent to the camera element. The fluorescently labeled particles may include a pathogen or bacteria, for example, *E. coli* bacteria.

In one embodiment, a fluorescent imager for use with a mobile device having a camera element includes a housing configured for securement to the mobile device; a sample holder disposed in the housing and configured to hold a sample; an excitation light source disposed in the housing an oriented to side illuminate the sample holder; a filter holder disposed in the housing and configured to hold filter media therein; and a lens disposed in the housing, wherein the housing is configured to attach to the mobile device to place the lens adjacent to the camera element.

In another embodiment, a method using the fluorescent imaging device includes loading a sample into the sample holder; illuminating the sample with the excitation light source; and acquiring one or more images with the camera element of the mobile device.

In another embodiment, a fluorescent imager for use with a mobile device having a camera element includes a housing configured for securement to the mobile device; a sample holder disposed in the housing; an excitation light source disposed in the housing an oriented to side illuminate the sample holder; a filter holder disposed in the housing and configured to hold filter media therein; and a lens disposed in the housing, wherein the housing is configured to attach to the mobile device to place the lens adjacent to the camera element. In one aspect, the sample holder may include a microfluidic flow cell. The housing may be permanently attached to the mobile device or, alternatively, the housing may be removeable from the mobile device.

In another embodiment, a method of using the fluorescent imager includes flowing a sample through the microfluidic flow cell, the sample containing cells or particles and a fluorophore configured to bind to at least some of the cells or particles; illuminating the sample with the excitation light source; and acquiring a plurality of consecutive image frames with the camera element of the mobile device. The plurality of consecutive image frames may comprise a movie clip. The cells or particles imaged in the movie clip may be tracked and/or counted. The cell count may be converted to a cell density in some embodiments which can then be used as a proxy for the diagnosis of various disease states and infections. Examples include leukemia, HIV, and bone marrow deficiencies. Further, the cells or particles that are captured within the movie may be labeled.

The integration of optofluidic fluorescent microscopy and flow cytometry on a mobile device with camera functionality (e.g., mobile phone) has been demonstrated using a compact, light-weight modular device that is relatively inexpensive. The microfluidic flow cells functions to hold the sample within an imaging volume and also acts as a multi-layered optofluidic waveguide and efficiently guides excitation light that is butt-coupled from the side facets of the microfluidic flow cell using a plurality of light emitting diodes (LEDs). The performance has been tested by measuring the density of white blood cells (WBCs) in whole blood samples, providing a good match to another commercially available hematology analyzer. Imaging performance has also been shown to demonstrate a fluorescent resolution of about 2 μm. The mobile device-enabled optofluidic imaging flow cytometer can be particularly useful for rapid and sensitive imaging of bodily fluids for, e.g., conducting various cells counts or for screening of water quality in resource-limited locations.

BRIEF DESCRIPTION OF THE DRAWINGS

FIG. 1A illustrates an exploded view of mobile device having a camera element and a fluorescent imager attachment device according to one embodiment.

FIG. 6A illustrates images taken of green and red fluorescent beads using a mobile phone based fluorescent imager device. Images A-1, B-1, and C-1 in FIG. 6A are green beads while images D-1, E-1, and F-1 in FIG. 6A are red beads. All of the images in FIG. 6A demonstrate ~20 μm resolution.

FIG. 6B illustrates the images of FIG. 6A after compressive decoding. Resolution is now improved to ~10 μm as seen by images C-2 and F-2 of FIG. 6B which is able to resolve closely spaced particles.

FIG. 6C illustrates 10× microscope objective images (NA=0.25) of the same samples acquired with a conventional fluorescent microscope. Note that because samples were suspended in solution, relative orientations might be slightly shifted in microscope comparison images.

FIG. 8A illustrates images of fluorescently labeled *Giardia Lamblia* cysts taken using the mobile phone based fluorescent imager device.

FIG. 8B illustrates 10× microscope objective images (NA=0.25) of the same *Giardia Lamblia* cysts samples acquired with a conventional fluorescent microscope.

FIG. 12A illustrates the imaging performance of the mobile phone based optofluidic fluorescent microscope for several sets of beads.

FIG. 12B illustrates, for comparison purposes, the same beads imaged by a conventional bench-top fluorescent microscope using a 40× (NA=0.6) microscope objective.

DETAILED DESCRIPTION OF THE ILLUSTRATED EMBODIMENTS

Figure 1B:
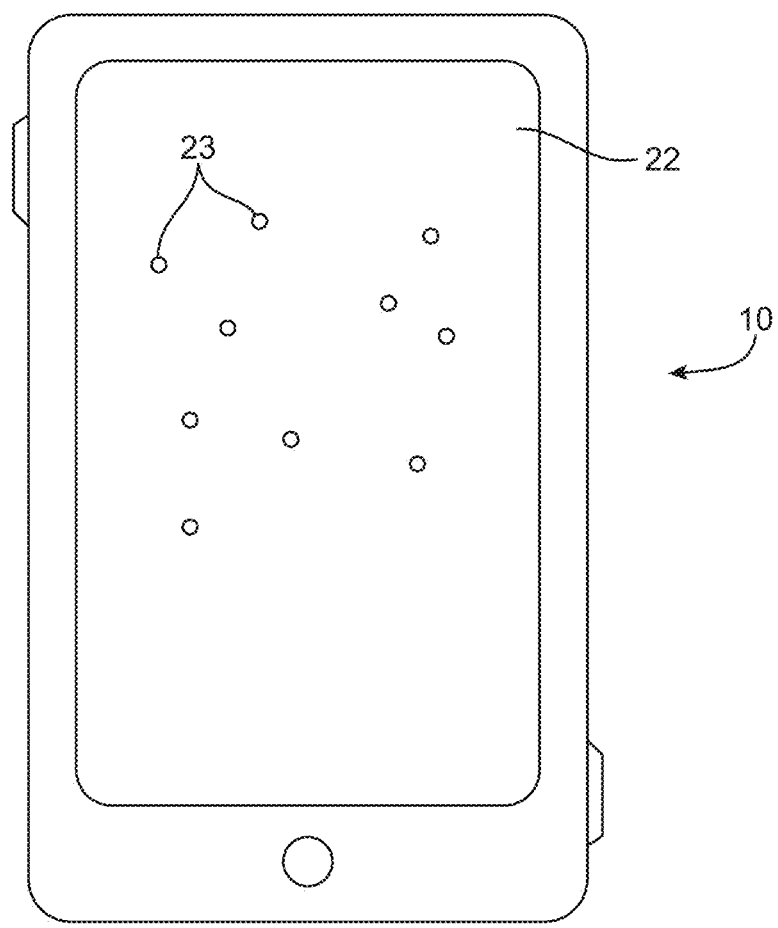
FIG. 1B is an image of a mobile device illustrating a screen containing images of objects thereon.

FIG. 1A illustrates a mobile device 10 having a camera element 12. The mobile device 10 may include a mobile phone, personal digital assistant (PDA), web camera (e.g., webcam) or the like that includes camera functionality. The camera element 12 which is seen in FIG. 1A generally includes a camera lens 13 along with internal camera components such as an image sensor 15 (shown in phantom) and other features typically found within mobile devices having camera functionality.

Still referring to FIG. 1A, a fluorescent imager 14 is provided that works in conjunction with the imaging capability of the mobile device 10. The fluorescent imager 14 includes a housing 16 that contains all the fluorescent imaging components. The housing 16 can be made from a durable yet lightweight material. Examples include polymer or plastic materials or even metal or metal alloys. The housing 16 contains a mounting portion 18 that may include a plurality of gripping elements 20 that are used to grip and thus secure the housing 16 to the mobile device 10. In this manner, the housing 16 is able to clip onto the mobile device 10 and can be removed from the same when needed. The gripping elements 20 may include snap-fit flanges or the like that partially wrap around the sides of the mobile device 10. Preferably, the gripping elements 20 are made such that the housing 16 can be slid or otherwise moved so as to align the optical path of the fluorescent imager 14 with that of the mobile device 10 (e.g., lenses of fluorescent imager 14 and lens 13 of mobile device 10 are substantially aligned).

The gripping elements 20 may be custom designed to a particular mobile device 10. For example, the configuration, location, and dimensions of the gripping elements 20 may be designed to match the particular physical dimensions of a phone. For example, the housing 16 of a fluorescent imager 14 may be designed with a mounting portion 18 and thus gripping elements 20 that are configured dimensioned to engage the unique edges and thicknesses of a particular phone type (e.g., IPHONE or SAMSUNG mobile phone). Alternatively, the mounting portion 18 and gripping elements 20 may be designed with a generic configuration that permits attachment to most models and makes of mobile devices 10. For instance, the gripping elements 20 may include a degree of flexibility that permit the housing 16 to be secured to mobile devices having different dimensions. The mounting portion 18 and gripping elements 20 are such that the housing 16 is configured to be repeatedly attached and removed from the mobile device 10. The fluorescent imager 14 can thus be mounted on the mobile device 10 when needed and simply removed from the mobile device 10 after use. Alternatively, in some embodiments, the fluorescent imager 14 may be permanently attached or otherwise secured to the mobile device 10.

FIG. 1B illustrates the side of the mobile device 10 that contains the screen 22. The screen 22 is used to display fluorescent images taken using the fluorescent imager 14. FIG. 1B illustrates a series of bright dots 23 against a generally darker background. The bright dots 23 represent the fluorescent cells or particles that are imaged by the fluorescent imager 14 and mobile device 10. The screen 22 may be used to interface with the mobile device 10 as is common with most mobile devices 10.

Figure 1C:
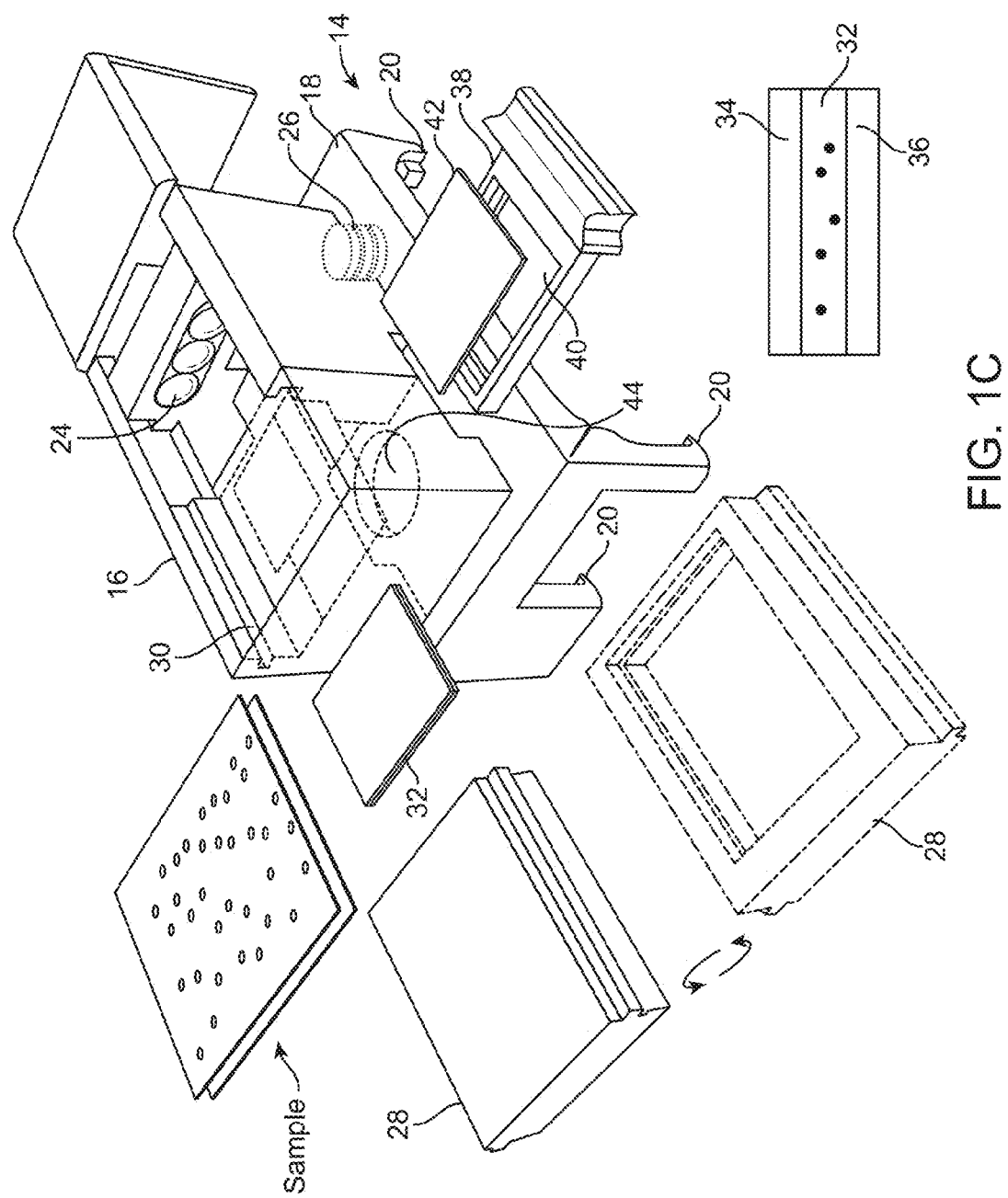
FIG. 1C illustrates an exploded view of a fluorescent imager according to one embodiment.

FIG. 1C illustrates an exploded view of the fluorescent imager 14. Located inside the housing 16 is an excitation light source 24 that is used as the fluorescent pump source. The excitation light source 24 may include one or more light emitting diodes (LEDs). The excitation light source 24 is powered by one or more batteries 26 also located within the housing 16 (cut away of portion of housing 16 is illustrated). The excitation light source 24, as explained below, is oriented to emit fluorescent excitation light that is generally perpendicular to the optical path between the camera lens 13 sample holder 28 that contains a sample therein. FIG. 1C illustrates a sample holder 28 in the normal orientation as well as in a flipped orientation. The sample holder 28 is configured to rest within housing 16 such that excitation light source 24 is butt coupled to the side sample holder 28. In this manner, the edge or side of the sample holder 28 acts as a waveguide for the pumped light emitted from the excitation light source 24. The sample holder 28 may be secured within the housing 16 on a support 30 which may take the form of a tray, ridge, platform or the like. The sample holder 28 may be any number structures used to hold a sample. These include an optically transparent slide (e.g., glass or plastic slide), cuvette, multi-layer waveguide, or even an array of capillary tubes.

In one preferred aspect, the sample holder 28 is a multi-layer waveguide that includes a three (3) layered refractive index structure. For example, the sample 32 may be sandwiched between opposing glass substrates 34, 36 (i.e., glass-sample-glass) surrounding by air on both sides. This structure acts as a multi-mode slab waveguide that has strong refractive index contrast at the air-glass interfaces (i.e., top and bottom surfaces). Because of this the pumped photos are tightly guided within this waveguide given the butt coupled, side illumination from the excitation light source 24. The refractive index contrast at glass-sample solution interfaces are much weaker compared to air-glass interfaces, which permits some of the pump photons to leak into the sample solution to efficiently excite e.g., labeled cells or pathogens suspended within the sample. A small gap on the order of a few micrometers to a few millimeters separates the excitation light source 24 from the side of the sample holder 28 when loaded in the housing 16.

Still referring to FIG. 1C, a moveable filter holder 38 is located within the housing 16. The filter holder 38 contains an aperture 40 therein for the passage of light but is able to retain a filter 42 thereon. The filter holder 38 is able to be slid in and out of the housing 16 so that different filters 42 may be loaded into the filter holder 38. In some embodiments, the filter holder 38 may be fixed in place. The filter 42 is made from a colored plastic material that contains a dye or other color component. Different filters 42 are able to transmit different wavelengths of light. Both the LEDs and the filter 42 can be easily changed for different excitation/emission colors, and therefore the platform is compatible with a wide range of fluorophores. The filters 42 are made of relatively inexpensive plastic material (Kodak Wratten Color Filter 12) that is sufficient to create the necessary dark-field background to detect the brighter fluorescent dots 23 within the image.

Because the excitation modes of the sample propagate perpendicular to the detection path of the fluorescent imager 14, ignoring scattering, the only detected photons would be the fluorescent emission coming from the excited samples. To eliminate detection of scattered pump photons (due to e.g., possible scratches on the surface of the glass sample or scattering from the cells/particles), this inexpensive plastic color filter 42 is also used to improve the dark-field condition.

The housing 16 further includes a lens 44 therein that is located within the optical path created between the sample holder 28 and the camera element 12 of the mobile device 10. The lens 44 is positioned adjacent to the lens 13 of the mobile device 10 when the housing 16 is mounted to the mobile device 10. The lens 44 functions as a de-magnifying lens. The focal length of the lens 44 may be larger than the focal length of the lens 13 of the mobile device 10 to create a demagnification between the sample plane and the imaging sensor plane. The de-magnification factor may be altered by changing the focal length of the lens 44 and is independent of the physical distance between lens 13 and lens 44.

Figure 1D:
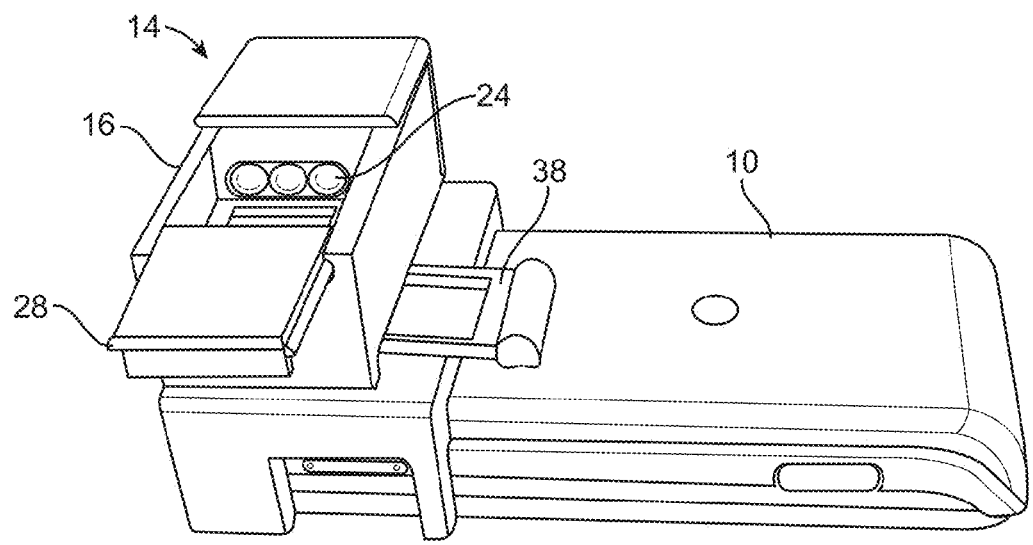
FIG. 1D illustrates a view of the fluorescent imager attachment secured to a mobile phone.

FIG. 1D illustrates a mobile device 10 having secured thereto the fluorescent imager 14. The sample holder 28 is seen partially loaded in the housing 16 thereby exposing the excitation light source 24, which in this embodiment, includes three (3) LEDs. Importantly, the fluorescent imager 14 may be repeatedly attached and detached to the mobile device 10 without the need for any fine alignment or tuning. In some embodiments, the mobile device 10 may include detents, ridges, or indicia that indicate where the fluorescent imager 14 should be secured to the mobile device 10. However, in other embodiments, the user simply locates the fluorescent imager 14 onto the mobile device 10 at a location that places the lens 44 substantially adjacent to the lens 13 contained in the mobile device 10. The fluorescent imager 14 is small and compact. For example, the fluorescent imager 14 may weigh less than about 20 grams (or in other embodiments less than 30 grams) and has a size that is less than about 100 $cm^3$ or in other embodiments less than 50 $cm^3$.

To use the imaging platform, a sample is loaded into the sample holder 28 which is then loaded into the housing 16. The sample contains cells, pathogens, particles of interest together with a fluorophore that binds to a target. The target may include a particular cell phenotype, pathogen, or a live or inanimate object that bears molecular moieties that bind to the fluorophore. The housing 16 of the fluorescent imager 14 is then secured to the mobile device 10 (of course, the housing 16 may first be secured to the mobile device 10 and the sample holder 28 then is subsequently loaded into the housing 16). The excitation light source 24 is then turned on so as to side illuminate the sample holder 28. Excitation photons enter the side of the sample holder 28 which acts as a waveguide and some of the excitation photons leak into the sample solution to efficiently excite the fluorophore-conjugated objects. The mobile device 10 is then placed into a camera mode using the conventional mobile device 10 user interface. An image is then obtained using the camera element 12 of the mobile device 10. The image generally includes a dark background with bright dots 23 that represent the location of the fluorophore-conjugated objects. Additional image frames may be captured by the mobile device 10 in a similar manner.

In one aspect, these images are then transmitted to a remote location for analysis or storage. For example, the mobile device 10 may be able to transmit the image(s) via a wireless network. The wireless network may include, for example, a mobile phone network used to carry voice and data. The wireless network may also include a local WiFi networks using the IEEE 802.11 or similar standard. Alternatively, the mobile device 10 may be coupled to a computer or other networked device via a cable or the like whereby data can then be transferred to a remote location. Analysis of the images may include counting of the number of bright dots 23 in the image which can then be translated into useful information such as cell counts, pathogen loading levels, and the like.

In one alternative aspect of the invention, the resolving power of the imaging platform is improved by applying a compressive sampling algorithm. Compressive sampling (also known as compressive sensing) is a recently emerging field that aims to recover a sparse function from many fewer measurements or samples than normally required according to the Shannon's sampling theorem. Details regarding compressive sampling may be found in the following publications which are incorporated by references as if set forth fully herein: E. J. Candes, J. K. Romberg and T. Tao, Comm. Pure Appl. Math., 2006, 59, 1207-1223; E. J. Candes and T. Tao, IEEE Trans. Inform. Theory, 2006, 52, 5406-5425; D. L. Donoho, IEEE Trans. Inform. Theory, 2006, 52, 1289-1306.

Figure 2:
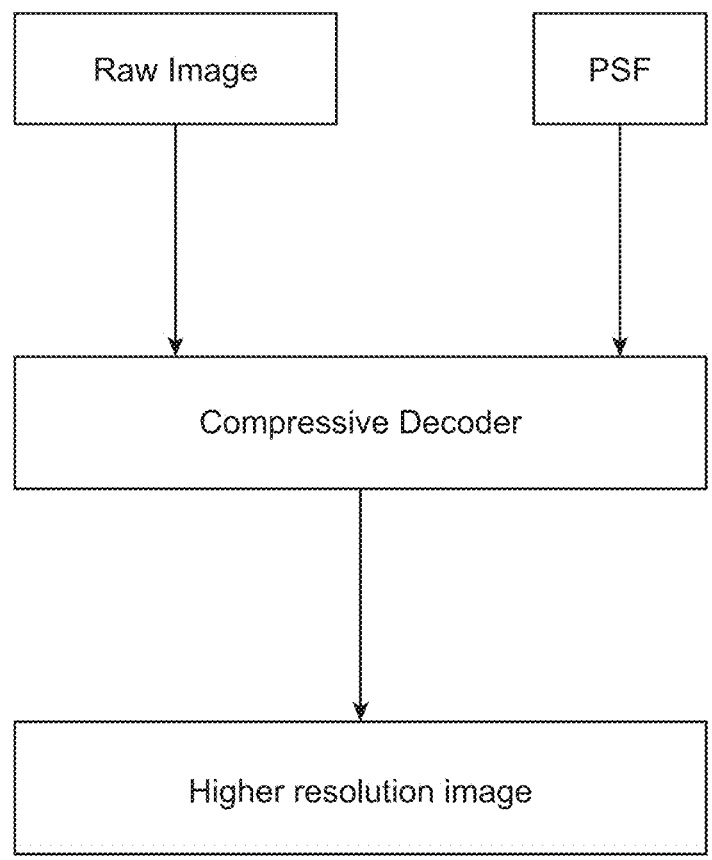
FIG. 2 illustrates a flow chart of operations involved in compressively decoding raw images into higher resolution images.

FIG. 2 graphically illustrates a process of using compressing decoding to improve the resolving power of the imaging platform. First, an incoherent point-spread function (PSF) of the imaging platform is generated. The PSF may be determined by recording fluorescent images of several isolated microspheres using the mobile device 10 with the fluorescent imager 14. The single particle fluorescent images are then aligned with respect to each other based on their center of mass calculations, details of which may be found in T. Su, S. O. Isikman, W. Bishara, D. Tseng, A. Erlinger and A. Ozcan, Opt. Express, 2010, 18, 9690-9711, which is incorporated by reference herein. After normalization of each image, by averaging these aligned particle images, an incoherent point-spread-function (PSF) is created for the mobile device 10 and fluorescent imager 14 system.

Figure 3A:
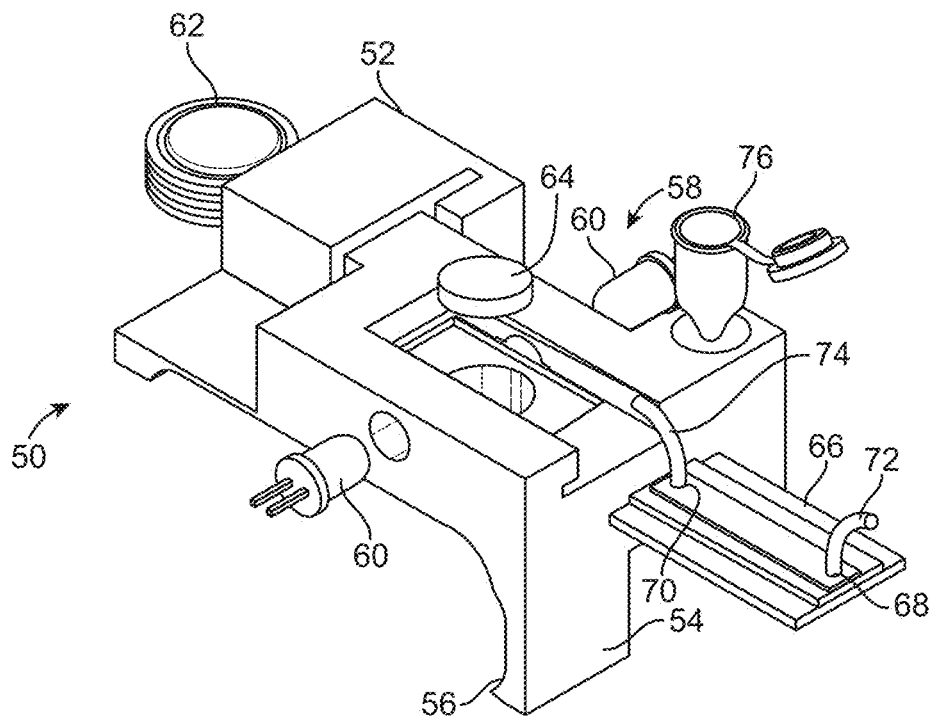
FIG. 3A illustrates a perspective view of a fluorescent imager according to another embodiment.
Figure 3B:
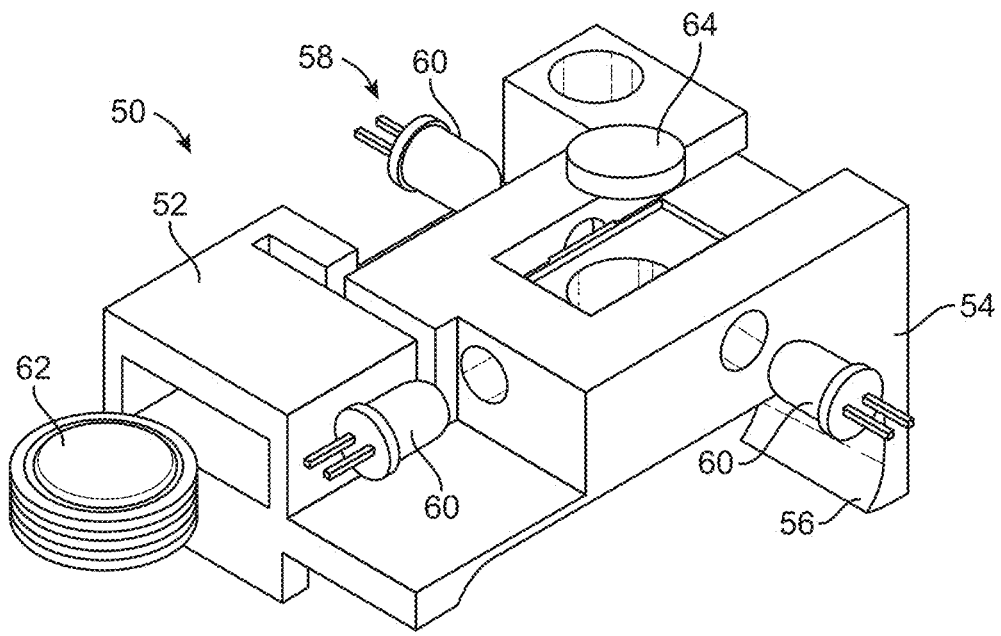
FIG. 3B illustrates another perspective view of the fluorescent imager of FIG. 3A.
Figure 4:
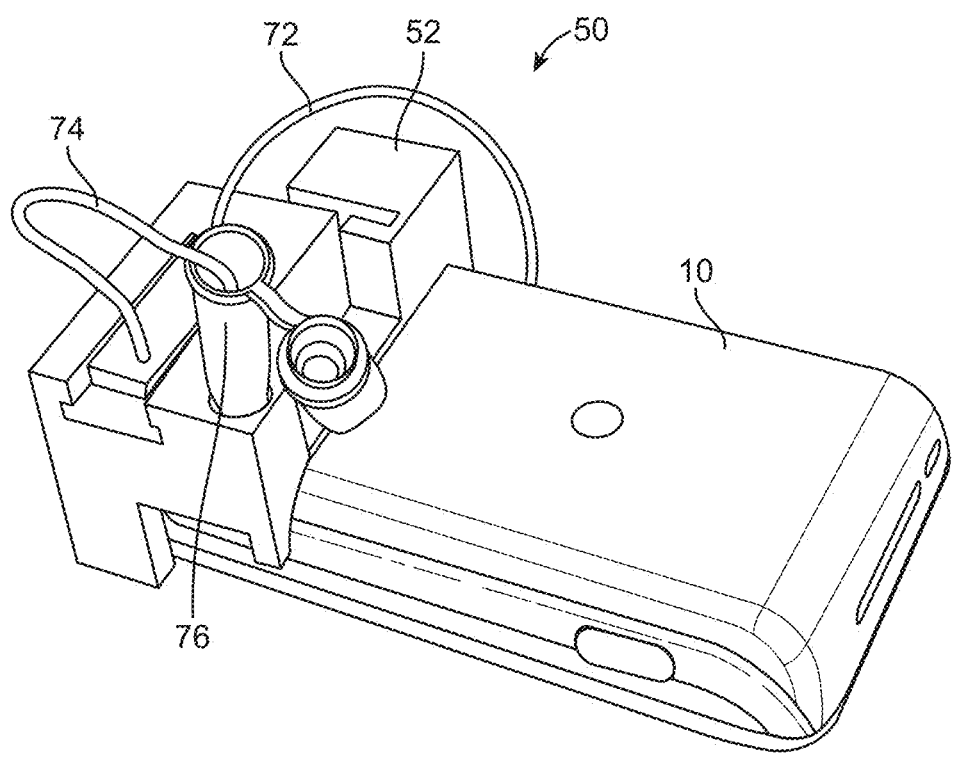
FIG. 4 illustrates a view of the fluorescent imager according to another embodiment secured to a mobile phone.

FIGS. 3A and 3B illustrate another embodiment of a fluorescent imager 50 for use with a mobile device 10 (mobile device 10 is illustrated in FIG. 4). In this embodiment, the fluorescent imager 50 includes a housing 52 that includes a mounting portion 54 that includes gripping elements 56 similar to those described in the prior embodiment. The fluorescent imager 50 includes an excitation light source 58 that includes multiple, opposing LEDs 60 that side-illuminate the sample. FIG. 3B illustrates one LED hidden from view in FIG. 3A (a total of three (3) LEDs are used to side illuminate the sample although more or less may be used). A power source such as a battery 62 is provided in the housing 52 to power the excitation light source 58. While not seen in FIGS. 3A and 3B, the fluorescent imager 50 includes a filter (moveable or fixed) holder that is configured to hold filters therein in the same manner as the prior embodiment. Thus, a filter is interposed in the optical path between the sample and the camera element 12 of the mobile device 10. A lens 64 (FIG. 3A) is provided in the housing 52 and operates as a focusing lens similar to lens 44 in the prior embodiment.

In the embodiment of FIGS. 3A and 3B, a microfluidic flow cell 66 (seen in FIG. 3A) is provided through which sample flows through. The microfluidic flow cell 66 may take the form of a microfluidic chip or the like. For example, the microfluidic flow cell 66 may be formed from a multi-layer structure in which a microfluidic channel is created therein that permits the passage of a fluid sample. The microfluidic flow cell 66 includes an inlet 68 and an outlet 70. Conduits 72, 74 may be coupled to both the inlet 68 and outlet 70, respectively. The conduit 72 coupled to the inlet 68 may be connected to a pumping source (not shown) such as syringe pump. The syringe pump (or other type of pump) continuously delivers sample solution of interest to the microfluidic flow cell 66 such at a fluorescent microscopic movie is obtained using the mobile device 10 of the flowing objects through the microfluidic flow cell 66. These objects, like the prior embodiment, may include cells, pathogens, particles, beads, or the like. Still referring to FIG. 3A, the conduit 74 coupled to the outlet 70 may be directed to empty sample solution into a sample collector 76. The sample collector 76 may be temporarily loaded into the housing 52 and can be removed when full or when otherwise desired for further processing and analysis of the sample.

The microfluidic flow cell 66 also acts as an optofluidic multi-mode slab waveguide, which has a three-layered refractive index structure (PDMS-liquid-glass) surrounded by air on both sides. Due to the stronger refractive index contrast of air-glass and air-PDMS interfaces compared to the glass-liquid or PDMS-liquid interfaces, this butt-coupled LED excitation light is tightly confined inside this multi-mode optofluidic waveguide structure which results in uniform and efficient pumping of the imaging volume within the microfluidic flow cell 66. In addition, since the excitation light propagates perpendicular to the fluorescence detection path, a simple plastic absorption filter such as filter 42 from the embodiment of FIG. 1C is sufficient to reject the scattered pump photons, creating, as desired, a strong dark-field background. Further, in this optofluidic design, the illumination light source (LEDs) and the plastic absorption filter can be easily changed to different colors and therefore the system is compatible with fluorophores that have different excitation/emission wavelengths.

FIG. 4 illustrates the fluorescent imager 50 of the alternative embodiment affixed to a mobile device 10. The sample collector 76 is illustrated in a loaded position within the housing 52 with the outlet conduit 74 positioned within the sample collector 76. In this alternative embodiment, the housing 52 has approximate dimensions of 3.5 cm×5.5 cm×2.8 cm. The fluorescent imager 50 is small and compact. For example, the fluorescent imager 50 may weigh less than about 20 grams (or in some preferred embodiments less than 30 grams) and has a size that is less than about 100 cm$^3$ (or in other embodiments less than 60 cm$^3$).

The fluorescent imager 50 can be repeatedly attached or detached to the mobile device 10 without the need for fine tuning of the alignment. The mobile device 10 includes camera element 12 that takes a plurality of consecutive image frames to form a movie clip or the like. In this regard, the mobile device 10 is able to capture a movie of the fluorescently labeled objects (e.g., cells, particles, beads) that bass through the microfluidic flow cell 66. The digital image frames of the fluorescent movies are then processed to count the fluorescently labeled objects therein which can then be used to determine or estimate the density of the target fluorescent objects within the sample volume. Imaging processing may take place using the internal processor(s) of the mobile device 10 or, alternatively, the image frames may be transferred to another computer or image processing device where object counting and tracking takes place. For example, the movie clip may be transmitted wirelessly to another computer where object counting and tracking is performed. The mobile device 10 may also be physically connected to a computer via a cable or the like for transfer of movie clips. Digital processing of the image frames may include detecting the total fluorescent radiation level due to fluorescently labeled specimens that pass through the microfluidic flow cell.

In one aspect, as explained below, the respective contour of each object is detected and the center of mass of each object is computed. The center of mass is then used to be the respective coordinate of each object. Each object is assigned a unique ID which is preserved through the analysis process for a given movie clip or sequence of images. For each subsequent frame in the movie clip, the object detection process is repeated. The coordinates of these newly detected objects are then compared to those of the object coordinates in the previous frame. Based on their proximity to the objects in the previous frame, the newly detected objects are assigned new IDs, or in other words, the coordinates of the particles are updated in the new frame, thus allowing objects to be tracked with unique IDs from the moment they first appear in the movie clip.

Optionally, in order to reduce errors in detection and tracking, a cascade of object counters in the manner of vertical counter lines may be established to monitor and count objects passing through each counter line independent of each other. By establishing multiple cascade lines in the image frames to track objects allows a more accurate count of the objects passing through the microfluidic flow cell 66. For example, counts can be averaged over multiple image frames (i.e., longer time periods).

Experiment

Embodiment No. 1

Here fluorescent microscopy on a mobile phone using the imaging platform of FIGS. 1A-1D using a compact (3.5×5.5× 2.4 cm) and light-weight (~28 grams) optical housing attachment to the existing camera-unit of the mobile phone. This platform achieves an imaging FOV of ~81 mm$^2$ with a raw spatial resolution of ~20 μm, which can further be improved to ~10 μm using digital signal processing of the captured fluorescent images based on compressive sampling as described herein. In this approach, the fluorescent sample is pumped using battery-powered light-emitting diodes (LEDs) that are butt-coupled to the sample from the side. This pump light is guided within the sample cuvette uniformly exciting the specimen of interest. The fluorescent emission from the sample is then imaged using a lens that is placed in front of the existing mobile phone camera lens. Because the excitation light is guided perpendicular to the detection path, a plastic color filter can be used to create the necessary dark-field background. This feature eliminates the use of expensive fluorescent filters (e.g., thin-film interference filters) that are used in conventional fluorescent microscopes.

There are several important features of this mobile phone based fluorescent imaging platform that make it especially suitable for global health applications. These features include the relative inexpensive nature of the components. Major components of the fluorescent imager attachment include a simple lens (cost: ~12 USD/piece), a plastic color filter (cost: ~1.1 USD/piece), 3 LEDs (cost: ~0.3 USD/piece), and a battery (cost: ~0.5 USD/piece), which make this fluorescent imaging platform on a mobile phone extremely cost-effective. Imaging throughput is also high in the platform. The large FOV (~81 mm$^2$) and the depth-of-field (>1-2 mm) of this platform permits imaging of >0.1 mL of sample volume, which would be important for high-throughput imaging of specially designed microfluidic channels for detection and quantification of e.g., rare cells or low concentration bacteria/pathogens. For example, the platform may be used to screen samples for bacteria such as *Escherichia coli* (*E. coli*). Finally, the imaging platform is compact and lightweight. The entire housing attachment to the mobile phone (which includes all the optical components, battery, as well as the mechanical components shown in FIGS. 1A-1D) weighs ~28 grams (~1 ounce) and has dimensions of ~3.5×5.5×2.4 cm. This compact and light-weight unit can be repeatedly attached and detached to the mobile phone body without the need for any fine alignment/tuning, making its interface fairy easy to operate even in resource limited settings.

While the features discussed above make this platform rather promising for telemedicine applications, a trade-off in spatial resolution has also been made in the design, i.e., in return for achieving a cost-effective and compact wide-field fluorescent imaging interface on a mobile phone, the spatial resolution is limited to ~10-20 µm. This, however, is still an acceptable resolution for several applications that demand rapid screening of large sample volumes of e.g., blood, urine, sputum or water. To demonstrate such opportunities, the performance of this wide-field fluorescent platform has been confirmed by successfully imaging labeled white-blood cells from whole blood samples, as well as water-borne pathogenic protozoan parasites such as *Giardia Lamblia* cysts. In addition, the performance of this platform has been confirmed by imaging fluorescent micro-particles in two different colors (i.e., red and green) and compared against conventional fluorescent microscope images of the same samples, validating the spatial resolution across an FOV of ~81 mm$^2$ As seen in FIG. 1D, the fluorescent microscopy platform is directly attached to the existing camera unit of the mobile phone with a compact and light-weight interface, which mainly includes three (3) LEDs, a simple lens, and a mechanical tray for holding a plastic color filter as illustrated in FIG. 1C.

For the mobile device, a Sony-Erickson U10i Aino™ was used as the starting base of the platform. However, it should be understood that the devices and methods described herein can easily be installed on various other mobile phones independent of the operating system or the communication protocol. This particular mobile phone has an ~8 Mpixel color RGB sensor installed on it, which was used to capture the fluorescent images of the samples.

The digital camera unit of the mobile phone has already a built-in lens in front of the CMOS chip, which has a focal length of f~4.65 mm. To image the fluorescent sample onto the CMOS sensor chip, another lens ($f_2$=15 mm) was placed (i.e., lens 44) in front of the existing camera lens, which creates a de-magnification of $f_2/f$=~3.2 between the sample plane (located at the focal plane of $f_2$) and the CMOS sensor plane. This de-magnification factor can easily be tuned by changing the value of $f_2$, and quite conveniently, it is independent of the physical distance between the two lenses, which makes it rather tolerant to vertical misalignments of the attached unit. Based on this imaging geometry, the effective pixel size at the sample plane becomes ~5-6 µm, which is in good agreement with the raw resolution of ~20 µm as demonstrated in FIG. 6. As will be detailed in the next sections, this raw resolving power can further be improved by another factor of ~2, without a trade-off in the imaging FOV.

Besides resolution and FOV, another important challenge in fluorescent microscopy is the rejection of the pump photons. Conventional fluorescent microscopes mostly utilize thin-film interference filters which are relatively expensive. In this mobile phone microscope design, to achieve a decent dark-field background without the use of such expensive filters, a different pumping scheme was used as illustrated in FIG. 1C, where the pump light (generated by 3 LEDs—Digikey Corp, Thief River Falls, Minn.) was actually coupled to the sample holder from the side using lens-free butt-coupling. Because of the large cross-section of the LED light, this coupling is quite insensitive to alignment, which makes it repeatable from sample to sample. The sample holder can be considered to be a multi-mode slab waveguide, which has a 3-layered refractive index structure (glass-sample-glass) surrounded by air on both sides. Such a waveguide has strong refractive index contrast at the air-glass interfaces (i.e., the top and the bottom surfaces), as a result of which the pump photons are tightly guided within this waveguide. On the other hand, the refractive index contrast at glass-sample solution interfaces are much weaker compared to air-glass interfaces, which permits some of the pump photons to leak into the sample solution to efficiently excite e.g., labeled cells/pathogens suspended within the sample. This excitation is fairly efficient and uniform, and is quite repeatable from sample to sample. The same principles also apply to the capillary based fluorescent imaging as demonstrated in FIG. 9, where the pump light is guided within the tube.

Because the excitation modes of the sample structure propagate perpendicular to the detection path of the fluorescent microscope, ignoring scattering, the only detected photons would be the fluorescent emission coming from the excited samples. To eliminate detection of scattered pump photons (due to e.g., possible scratches on the surface of the glass sample or scattering from the cells/particles), an inexpensive plastic color filter (Kodak Wratten Color Filter 12) is also used to improve the dark-field condition. Experimental results presented herein illustrate the success of this approach despite its simple, compact and cost-effective design installed on a mobile phone unit having a camera.

With this imaging architecture, the acquired fluorescent images are stored at the mobile phone memory in .jpg format, and can be viewed through the screen of the mobile phone after appropriate digital zooming. These .jpg files (typically ~2-3 MB for an ~8 Mpixel image) can also be transferred to a computer (e.g., through memory cards or using wireless communication) for further digital processing, including but not limited to compressive decoding to resolve some of the overlapping fluorescent signatures in the raw images. If a smaller FOV is acceptable, the mobile phone also permits the capture of e.g., ~3 Mpixel images (corresponding to an FOV of ~20-30 mm$^2$) which now can be stored with ~1 MB.

Figure 5:
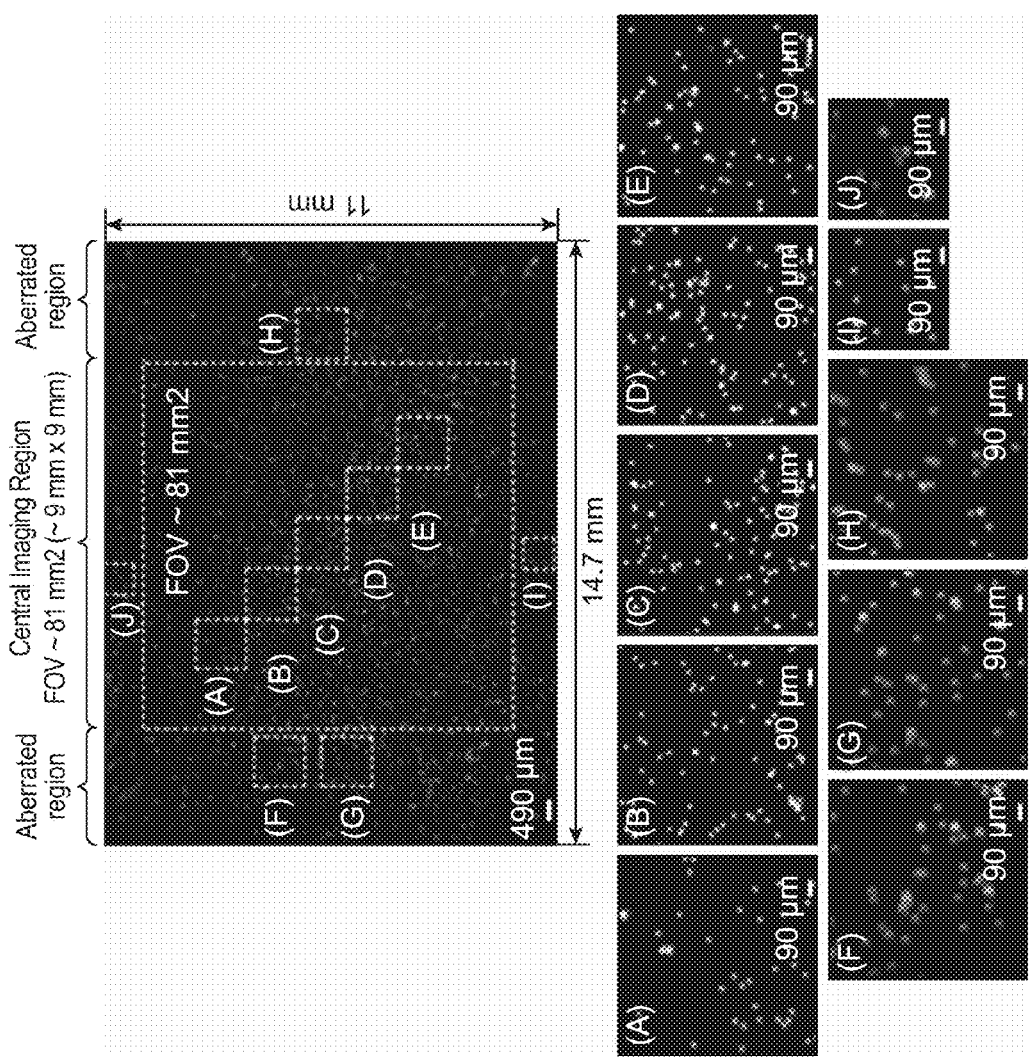
FIG. 5 illustrates images taken of fluorescent beads (10 μm diameter; excitation/emission: 580 nm/605 nm) from a fluorescent imager secured to a mobile phone. The central field-of-view of the image is ~81 mm$^2$. Also illustrated are zoomed frames A-J below the main image.

The fluorescent imaging capability of this platform was first demonstrated using fluorescent micro-beads (with a diameter of 10 µm) at two different emission wavelengths, i.e., 515 nm and 605 nm as shown in FIGS. 5-6. Fluorescent beads with 10 µm diameter (red beads: product #F8834 excitation/emission 580 nm/605 nm; green beads: product #F8836: excitation/emission 505 nm/515 nm) were purchased from Invitrogen (Carlsbad, Calif.). To prepare the fluorescent bead samples, 10 µL of beads was mixed with 40 µL of DI water. Then 10 µL of this mixture was placed between two glass slides (12.5 mm×17 mm) using a micropipette. Alternatively, simple capillary action was also used to load the sample into capillary tubes as in FIG. 9. The sample was then inserted into the sample tray and slid into the mobile phone attachment (FIG. 1C and FIG. 1D).

To characterize the FOV of this platform, red fluorescent beads (between two microscope slides) were imaged as illustrated in FIG. 5 over an area of 14.7 mm×11 mm. Toward its edges, this imaging area has aberrations (see e.g., FIG. 5; zoomed frames F-J), and therefore only the central region spanning an area of ~9 mm×9 mm exhibited a decent imaging performance, creating an FOV ~81 mm² as indicated with the dashed square in FIG. 5. Due to its large FOV and low numerical aperture, this mobile phone based fluorescent microscopy platform has the capability to screen large sample volumes (>0.1 mL) which could be especially important for rapid screening of e.g., blood, urine, saliva, water etc. While the aberrated regions (e.g., FIG. 5; zoomed frames F-J) look significantly distorted when compared to the central imaging area (e.g., FIG. 5; zoomed frames A-E), for various cell counting or detection applications in resource-limited settings, such aberrated regions could still be useful, which would potentially further increase the imaging area beyond 81 mm²

Next, a series of experiments were performed to characterize the spatial resolution of the fluorescent imaging platform using green and red fluorescent beads (10 µm diameter). FIGS. 6A-6B illustrates the imaging performance of the mobile phone microscope for several sets of beads. FIG. 6A illustrate the raw mobile phone images while FIG. 6B illustrates mobile phone images that have undergone compressive decoding. The same samples were also imaged by a conventional fluorescent microscope using a 10× microscope-objective (numerical aperture 0.25) as shown in FIG. 6C. Based on these results, using the raw mobile phone images, the imaging platform can resolve two beads that are separated by ~20 nm (center-to-center). This resolving power can be further improved through digital signal processing of the captured fluorescent images based on compressive sampling theory.

By using an l1-regularized least squares optimization algorithm, one can achieve a spatial resolution that is much better than the incoherent point-spread function of the system would normally permit. This approach is especially powerful for imaging of randomly distributed cells/bacteria (suspended in a solution or captured within a microfluidic channel) since the sparsity constraint of compressive sampling is then rather easy to satisfy for practical samples of interest.

Here, compressive sampling was used to improve the resolving power of the raw fluorescent images by a factor of ~2 (See FIG. 6B). As part of the compressive sampling process, fluorescent images were first recorded of several isolated microspheres (4 and 10 nm diameter) using the mobile phone imaging platform. These single particle fluorescent images were then aligned with respect to each other based on their centers of mass calculations. After normalization of each image, by averaging these aligned particle images, an incoherent point-spread-function (PSF) was created for the mobile phone microscope. With this well-defined PSF, one can easily calculate the projected image on the CMOS sensor for any arbitrary distribution of fluorescent points within the sample plane. Using this principle, an iterative algorithm was used to minimize the differences between the theoretically projected and the measured fluorescent images while maintaining the sparsity constraint for the fluorescent channel. Mathematically, this recovery process can be expressed as an l1-regularized least squares problem, such that:

$$\hat{c} = \mathrm{argmin} \|I - M \cdot \bar{c}\|_2^2 + \beta \cdot \|\bar{c}\|_1$$

where $\beta > 0$ is a regularization parameter; I is the detected raw fluorescent image at the sensor-array (in a vector form); M represents the 2D convolution matrix based on the incoherent PSF of the imaging system; $\bar{c}$ is the theoretical fluorescent source distribution that creates the image at the sensor plane; and $$\|\bar{x}\|_p = \left(\sum_{i=1}^{n} |x_i|^p\right)^{1/p}$$

represents the $l_p$ norm of $\bar{x}$. Based on this numerical recipe, the raw fluorescent images acquired by the mobile phone microscope was successfully decoded as illustrated in FIG. 6B. The decoded mobile phone images show that two (2) beads having a center-to-center distance of ~10 nm (that could not be resolved in the raw mobile phone images) are now digitally resolved as illustrated in FIG. 6B (image C-2 and F-2). It should be emphasized that even though this resolving power (~10 µm) is fairly modest, because of the large FOV of this platform (~81 mm²), it is still rather useful for various cell/pathogen detection and quantification applications, involving e.g., bodily fluid analysis in remote locations.

Finally, it should be noted that other numerical approaches can also be used for such a reconstruction task. For example, Lucy-Richardson deconvolution algorithm can work very well with both sparse and non-sparse objects. However, the resolution that it can achieve with sparse objects is limited due to the fact that the prior knowledge of sparsity in the fluorescent object distribution is not fully utilized during the reconstruction process.

Following these characterization experiments, the feasibility of using the mobile phone-based fluorescent microscopy platform was tested to image labeled cells in whole blood samples. White blood cells that were labeled with STYO®16 nucleic acid staining were imaged. These labeled white-blood cells were excited with blue LEDs (470 nm peak wavelength) and were imaged using the mobile phone based microscope, the results of which are illustrated in FIGS. 7A-7D. For white blood cell imaging, 1× red blood cell lysis buffer (product #00-4333) was purchased from eBioscience, Inc (San Diego, Calif.) and stored at 4° C. SYTO®16 green fluorescent nucleic acid stain (product #S7578, excitation/emission 488 nm/518 nm (+DNA) and 494 nm/525 nm (+RNA)) was purchased from Invitrogen (Carlsbad, Calif.). To prepare labeled white-blood cell samples, 1 mL of red blood cell lysis buffer was added to 200 µL of whole blood and incubated for 3 minutes. The lysed blood sample was then centrifuged and the white-blood cell pellet was re-suspended in 200 µL of PBS. Then 5 µL 1 mM STYO®16 solution was added to this 200 µL white blood cell sample and incubated in dark for ~30 minutes. After this incubation, the sample was centrifuged again. Supernatant was removed and the labeled white-blood cell pellet was re-suspended in PBS buffer. This labeled white blood cell solution was then placed between two glass slides (12.5 mm×17 mm) and was imaged using the mobile phone fluorescent microscope.

Figure 7A:
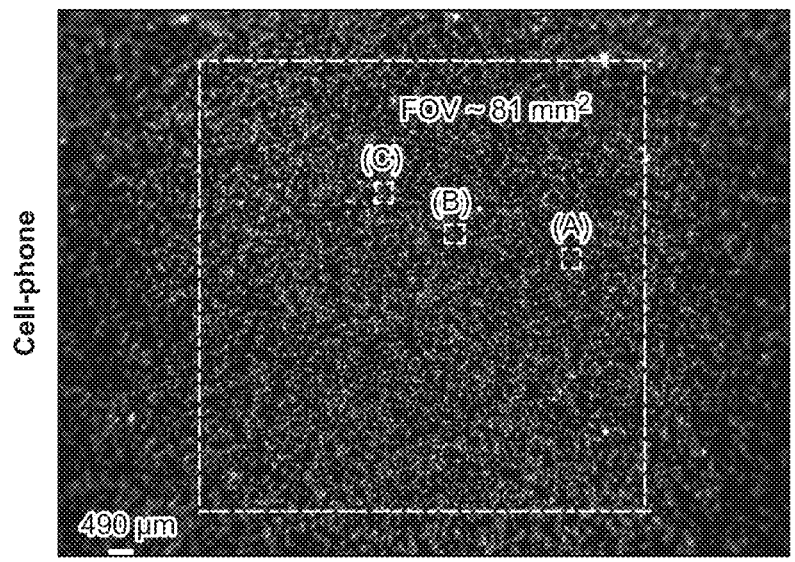
FIG. 7A illustrates a ~81 mm$^2$ FOV image of fluorescently labeled white blood cells taken using the mobile phone based fluorescent imager device.
Figure 7B:
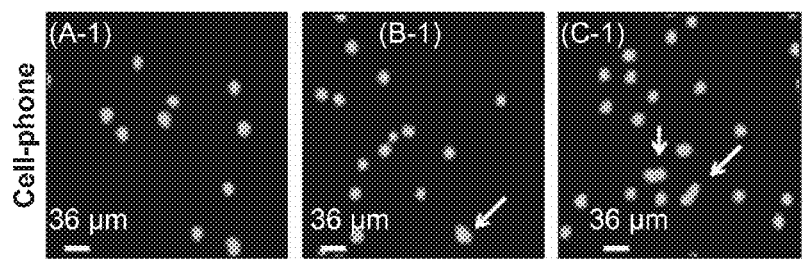
FIG. 7B illustrates zoomed frames A, B, and C taken from FIG. 7A.
Figure 7C:
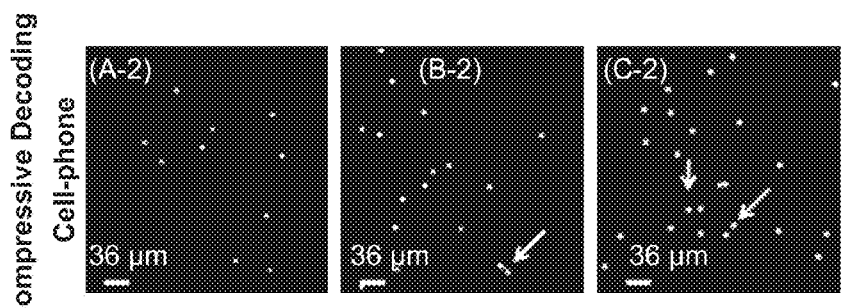
FIG. 7C illustrates the images of FIG. 7B after compressive decoding.
Figure 7D:
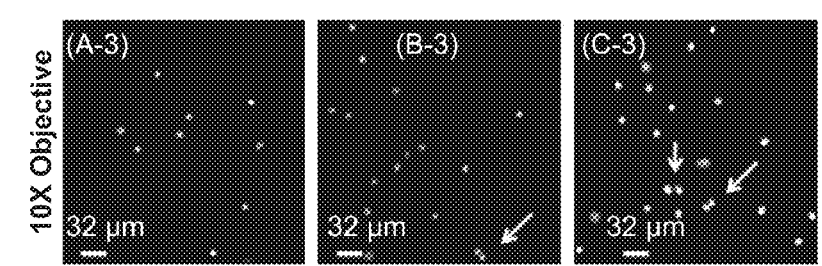
FIG. 7D illustrates 10× microscope objective images (NA=0.25) of the same white blood cell samples acquired with a conventional fluorescent microscope.

FIGS. 7B and 7C are digitally cropped from the central FOV of the mobile phone fluorescent image, showing raw signatures of the labeled white-blood cells. For comparison purposes, the same zoomed regions of the sample were also imaged using a conventional fluorescent microscope (10× microscope objective) as shown in FIG. 7D, which all provide a good match to the mobile phone fluorescent images. To further improve image quality, images were compressively decoded (FIG. 7C) to digitally arrive at higher resolution images which clearly demonstrate the improved resolving power similar to FIG. 7D (see e.g., the closely spaced white-blood cells as pointed by white arrows in FIG. 7C (images B-2 and C-2) and FIG. 7D (images B-3 and C-3).

The potential application of this mobile phone based fluorescent imaging system for water quality monitoring was also investigated. For this purpose, *Giardia Lamblia* was chosen as the model system in this study because it is one of the most widely found pathogen that exists in water sources. Because it only takes ingestion of as few as ten (10) *Giardia Lamblia* cysts to cause an infection, it is highly desirable to have a detection method that can rapidly identify low concentration cysts in drinking water. *Giardia Lamblia* cysts were purchased from WaterBorne Inc. (New Orleans, La., USA). The initial *Giardia Lamblia* cyst concentration was ~5×10$^6$ parasites/mL which were all fixed in 5% Formalin/PBS at pH 7.4/0.01% Tween-20. 100 μL of this sample was centrifuged and the pellet was re-suspended into 100 μL PBS buffer. 2.5 μL 1 mM SYTO®16 solution was added to this 100 μL *Giardia Lamblia* sample and incubated in dark for ~30 minutes. After this incubation, the sample was centrifuged and the pellets were re-suspended in PBS buffer. The *Giardia Lamblia* sample was then placed between two glass slides (12.5 mm×17 mm) and was imaged using the mobile phone fluorescent microscope. FIG. 8 (images A-1, B-1, C-1) illustrates raw mobile phone fluorescent images of *Giardia Lamblia* cysts that were labeled using SYT® 16. These mobile phone images were digitally cropped from a large FOV (~81 mm$^2$), and for comparison purposes, the same regions of interest were also imaged using a conventional fluorescent microscope (10× microscope-objective), seen in FIG. 8B (images A-2, B-2, C-2) which very well matched to the mobile phone imaging results.

As discussed herein, the mobile phone fluorescent microscopy platform has the capability to rapidly image large samples volumes of e.g., >0.1 mL. In addition to this, fluorescent labeling can also provide high specificity and sensitivity for detection of pathogenic parasites at low concentration levels, all of which make the mobile phone fluorescent microscope a promising tool for monitoring of water-quality in resource limited environments.

Figure 9:
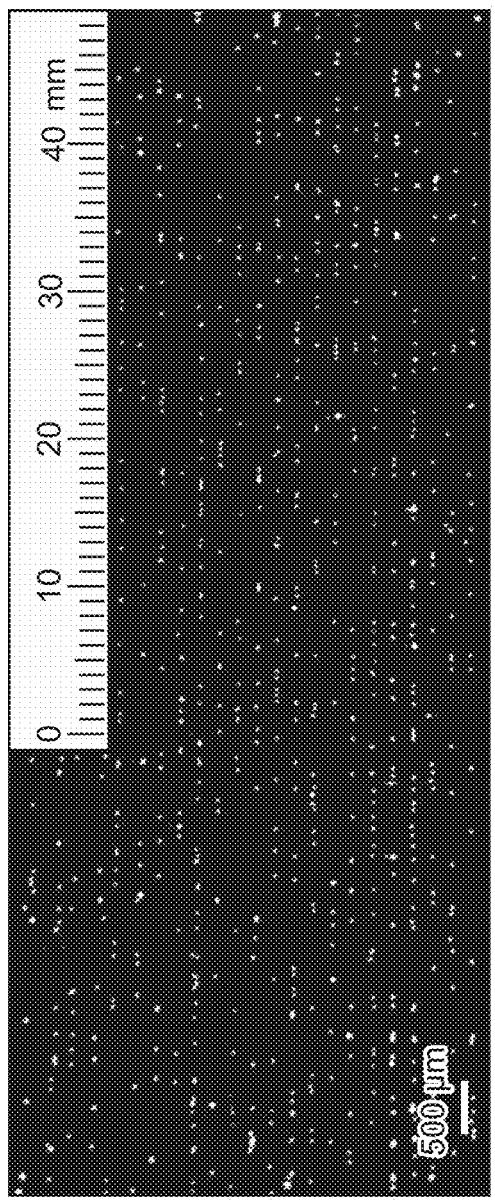
FIG. 9 illustrates 10 μm fluorescent beads loaded into several capillary tubes in parallel and imaged with the mobile phone based fluorescent imager device. Each capillary, when loaded with the sample solution, acts as a waveguide for pump photons, such that efficient excitation of the samples could be achieved. The inset figure at the top corner illustrates one of the capillaries used in this work (100 µm inner diameter; 170 µm outer diameter).

An alternative sample handling method involves the use of capillary tubes in the mobile phone microscopes. Rather than using planar substrates, in this embodiment, the mobile phone based fluorescent microscope can also image samples that are loaded into capillary tubes through simple capillary action. The excitation of the specimen within such capillary tubes shares the same approach that was previously used, such that the pump can be guided within the capillary which acts as a waveguide once loaded with a sample solution. This waveguide, even though it has a lower refractive index at the core, permits efficient excitation of the labeled objects within its core as illustrated in FIG. 9. Such a simple capillary based sample preparation approach could be rather convenient to use especially in remote locations where even basic laboratory instruments might not be readily available.

Experiment

Embodiment No. 2

The integration of an optofluidic fluorescent cytometry platform onto a mobile phone is demonstrated using compact and cost-effective optical attachments. In this design, the sample solution of interest is continuously delivered/pumped to the imaging volume using a disposable microfluidic flow cell (i.e., microfluidic channel). This microfluidic device assembly is placed above a separate inexpensive lens that is put in contact with the existing camera unit of the mobile phone as seen in FIG. 4 such that the entire cross-section of the microfluidic device can be mapped onto the CMOS sensor-chip of the mobile phone camera. Once inserted into the mobile phone based imaging flow cytometer, each microfluidic device is pumped from the side by light emitting diodes (LEDs) using simple butt-coupling, i.e., without the use of any bulky light-coupling optics or lenses as illustrated in FIG. 3. This pumped light is then guided within the cross-section of the microfluidic device (which acts as a multi-layered optofluidic waveguide composed of Poly(dimethylsiloxane)-liquid-glass interfaces surrounded by air) uniformly exciting the labeled specimens within the imaging volume. Because the guided excitation light propagates perpendicular to the detection path, this optofluidic pumping scheme permits the use of an inexpensive plastic absorption filter to create the dark-field background that is required for fluorescent imaging. With this optofluidic design, the sample solution of interest is continuously delivered to the imaging flow cytometer using e.g., a simple syringe pump, such that a fluorescent microscopic movie of the flowing particles or cells can be acquired using the mobile phone camera unit. The digital frames of these fluorescent movies are then rapidly processed to determine the count of labeled particles/cells, which can be used to estimate the density of the target fluorescent objects within the sample solution.

The performance of this mobile phone-based fluorescent imaging cytometer platform has been tested by measuring white blood cell density of human blood samples, the results of which provided a good agreement with a commercially available hematology analyzer (Sysmex KX-21N). In addition, the imaging performance of the mobile phone-based fluorescent microscopy platform has demonstrated ~2 μm spatial resolution with the same optofluidic design.

Poly(dimethylsiloxane) (PDMS) was purchased from Dow Corning (USA). SYTO®16 green fluorescent nucleic acid stain (product #S7578, excitation/emission 488 nm/518 nm (+DNA) and 494 nm/525 nm (+RNA)) and fluorescent beads (yellow-green fluorescence: excitation/emission 505 nm/515 nm) with 4 μm diameter (product #8859), 2 μm diameter (product #8827), and 1 μm diameter (product #13081) were purchased from Invitrogen (Carlsbad, USA). 1× Phosphate Buffered Silane (PBS) buffer (product # BP 2438-4) and microscope slides (product #12-5500) were purchased from Fisher Scientific (Pittsburgh, Pa., USA). Harris Uni-Core hole puncher was purchased from Ted Pella (Redding, Calif., USA). High frequency plasma generator (Model BD-10 AS) was purchased from Electro-Technic Products Inc. (Chicago, Ill., USA). Tygon tubing (ID: 0.01 inch/OD: 0.03 inch) (product #06418-01) was purchased from Cole-Parmer (Vernon Hills, Ill., USA). Plano convex lens (f=0.6 mm) (product # NT45-588) and yellow Kodak Wratten color filter (product # NT54-467) were purchased from the Edmund Optics (Barrington, N.J., USA). Aspherical lens (f=4.5 mm) (product # C230TME-A) was purchased from Thorlab (Newton, N.J., USA).

Microfluidic Device Fabrication and Preparation

PDMS based microfluidic devices were fabricated using standard soft lithographic techniques. See e.g., Mcdonald, J. C., and Whiteside, G. M., *Acc. Chem. Res.*, 2001, 35, 491-499, incorporated by reference as if set forth fully herein. Photoresist (SU-8) was spin-coated on a silicon wafer with an initial ramp of 500 rpm at 100 rpm second$^{-1}$ acceleration and kept constant for 10 seconds, followed by another ramp of 3000 rpm at 300 rpm second$^{-1}$ acceleration and kept constant for 30 seconds. After the resist was applied to the wafer surface, it was soft-baked with two sequential steps at 65° C. for 3 minutes and at 95° C. for another 9 minutes on a hotplate to evaporate the solvent and densify the film. To pattern the film with desired structures, UV exposure was applied to the coated substrate through a transparency mask (i.e., designed with AutoCAD and printed by CAD/Art Services Inc.) at 8 mW cm$^{-2}$ for 40 seconds on a mask-aligner (Karl Suss). Following the UV exposure, post-exposure bake was applied to the sample with two sequential steps at 65° C. for 2 minutes and at 95° C. for 7 minutes on a hotplate to selectively cross-link exposed parts of the photoresist. The patterned substrate was then developed by an SU-8 developer for 6 minutes to dissolve unexposed areas. Following development, the final substrate was rinsed with isopropyl alcohol (IPA) and then dried with a gentle nitrogen gas stream.

The PDMS prepolymer mixture (PDMS prepolymer: curing agent (v:v)=10:1) was poured onto the mold and degassed at room temperature for half an hour. Then it was baked at 70° C. for an hour. After curing, the PDMS was peeled off from the mold and holes were punched to form the inlet and outlet. The PDMS and glass slide (1 mm thick) were simply cleaned with soap water first and then they were treated with the high frequency plasma generator for 15 seconds. Immediately after plasma treatment, the PDMS was bonded to the glass substrate to be baked at 70° C. for another hour to strengthen the bonding. Finally, the tygon tubing (inner diameter: 0.01 inch) was inserted into the chip inlet/outlet and sealed with epoxy. The dimensions of the microfluidics chamber were 44 μm×3 mm×15 mm (height×width×length). Due to the final step of high temperature baking, the PDMS-glass chip interior surface becomes hydrophobic. In order to reduce the non-specific cell adsorption to the surface and bubble generation in the chamber, the microfluidic chamber was treated with plasma generator for 1 minute before each experiment.

Fluorescent Bead Sample Preparation

To prepare the fluorescent bead samples, 10 μL of beads (4 μm, 2 μm or 1 μm diameter) was mixed with 40 μL of deinoized (DI) water. Then 10 μL of this mixture was sandwiched between two glass slides (12.5 mm×17 mm) using a micropipette. This sample was inserted into the sample tray and slid into the mobile phone attachment for imaging.

Fluorescent Labeling of White Blood Cells in Whole Blood

To start with, SYTO®16 was warmed to room temperature and then briefly centrifuged in a micro-centrifuge tube to bring the dimethyl sulfoxide (DMSO) solution to the bottom of the vial. Whole blood sample was gently rotated and mixed well. Following this, 20 μL SYTO®16 was pipetted from the supernatant and added to 200 μL whole blood. This mixture was then incubated in dark for ~30 minutes. To avoid cell sedimentation, the sample was gently rotated during incubation. No red blood cell lysing step was performed. In addition, because the intrinsic fluorescence quantum yield of SYTO®16 is extremely low (<0.01), the unbound SYTO®16 was not separated from the whole blood after incubation. This labeled whole blood sample was directly diluted 10 fold with PBS buffer and was continuously delivered/pumped into the flow cell (microfluidic chip) through a syringe pump with a typical flow rate of ~1 μL min$^{-1}$ During the experiment, the blood sample vial was slowly agitated to avoid sedimentation of cells.

Design of the Imaging Platform

Experiments were conducted using the Sony-Erickson U100 AINO as the base mobile phone device for the optofluidic fluorescent microscopy and cytometry unit. This mobile phone has an 8 Mpixel color RGB sensor installed on it, which is used to capture fluorescent images/movies of the specimens. In addition, the camera has a built-in lens in front of the CMOS sensor of mobile phone, which has a focal length off ~4.65 mm.

To build an optofluidic fluorescent microscopy unit on this mobile phone, a single inexpensive lens with a focal length of $f_2$ (typically varying between 0.6 mm and 10 mm) was directly placed in front of the existing camera lens of the mobile phone as shown in FIGS. 3 and 4. This imaging geometry gives a magnification of $f/f_2$ between the sample plane (located at the focal plane of $f_2$) and the CMOS sensor. Depending on the application and its requirements on resolution and field-of-view (FOV), different magnification factors can be achieved by varying $f_2$ value. Note also that this magnification factor is theoretically independent of the distance between the two lenses, which makes alignment of the attachment to the mobile phone rather easy.

In order to increase the imaging throughput in the fluorescent cytometry platform unit magnification was used such that an aspherical lens with $f_2$=4.5 mm and 0.55 numerical aperture (NA) was placed in front of the existing mobile phone camera lens as shown in FIG. 3 (lens 64). For achieving higher spatial resolution in the optofluidic design, however, a plano-convex lens was used with $f_2$=~0.6 mm such that a magnification of ~7.8× was achieved, which improved the resolution down to ~2 μm in fluorescent imaging mode.

As for excitation light, the optofluidic fluorescent imaging cytometry unit utilizes blue LEDs that are directly butt-coupled to a microfluidic chip as illustrated in FIG. 3. Apart from continuously delivering the labeled specimens to the imaging volume, this microfluidic chip also acts as an optofluidic multi-mode slab waveguide, which has a 3-layered refractive index structure (PDMS-liquid-glass) surrounded by air on both sides. Due to the stronger refractive index contrast of air-glass and air-PDMS interfaces compared to the glass-liquid or PDMS-liquid interfaces, this butt-coupled LED excitation light is tightly confined inside this multi-mode optofluidic waveguide structure which results in uniform and efficient pumping of the imaging volume within the microfluidic flow cell. In addition, since the excitation light propagates perpendicular to the fluorescence detection path, a plastic absorption filter is sufficient to reject the scattered pump photons, creating, as desired, a strong dark-field.

During flow cytometry measurements, the Near High Definition (nHD) mode of the mobile phone was used to record fluorescent videos of the flowing specimens, which provided a resolution of 640×352 pixels per frame at a frame rate of ~7 frames per second (fps). In these flow cytometry experiments, the microfluidic chip was connected to a syringe pump through tygon tubing and fluorescently labeled samples were pumped into the microfluidic chamber continuously at a typical flow rate of ~1 μL min$^{-1}$ Digital processing of these fluorescent video frames was performed to automatically count the labeled cells/particles and then calculate their density for a given sample.

For imaging experiments where the spatial resolution of the optofluidic mobile phone attachment was quantified, the objects were kept stationary (i.e., without any fluidic flow) such that conventional fluorescent microscope images of the same samples can be obtained for comparison purposes. In this static microscopy mode, the fluorescent images captured by the optofluidic platform were stored at the mobile phone memory in jpg format, and could be viewed through the mobile phone screen directly. These jpg files (typically ~3-4 MB for an ~8 Mpixel image) can also be transferred to a computer (e.g., through memory cards or using wireless communication) for further digital processing or analysis.

Digital Analysis of Fluorescent Flow Videos

Video processing was used to count the labeled cells/particles passing through the microfluidic flow cell (i.e., microfluidic chip). Starting with the first frame, every visible fluorescent micro-particle is detected using the contour detection algorithm. Particular details regarding the contour detection method may be found in Suzuki, S., and Abe, K, Comput. *Vis. Graph. Image Process.*, 1985, 30, 32-46 which is incorporated herein by reference. For every detected contour, the center of mass is computed and is thereon assumed to be the coordinates of the particle. Each particle is then assigned a unique ID which is preserved throughout the analysis process for a given video stream. For each subsequent frame in the video, the particle detection process is repeated. The coordinates of these newly detected particles are then compared to those of the particle coordinates in the previous frame. Based on their proximity to the particles in the previous frame, the newly detected particles are assigned new IDs, or in other words, the coordinates of the particles are updated in the new frame, thus allowing particles to be tracked with unique IDs from the moment they first appear in the video.

In order to reduce errors in detection and tracking, the values were averaged over multiple frames (i.e. longer time periods). To do this, a cascade of counters was established, such that each virtual counter line monitors the particles that go through it independent of the others. Setting up multiple cascade lines to track the particles allows a more accurate count of the number of cells passing through the microfluidics chamber. It should be noted that the tracking algorithm used in this work is kept simple since the most important parameter for this work is the count of cells per unit time of flow. However, in more complicated settings different components of the algorithms need to be adapted to cope with the added complexities. For instance in cases where the physical patterns of the particle flow also need to be measured and tracked as a function of time/flow, a more complicated tracking algorithm can be used by e.g., addition of Kalman filtering.

To demonstrate the operation of the mobile phone optofluidic cytometry platform, white blood cells (WBCs) in human whole blood samples were chosen as the model system. White blood cells density in whole blood is routinely tested for clinical diagnosis of various diseases, including infections, leukemia, HIV, and bone marrow deficiencies. To test the flow cytometry platform on the mobile phone, white blood cells in fresh whole blood samples were labeled with SYTO®16 fluorescent dyes and diluted as described above without lysing red blood cells. These 10× diluted and labeled whole blood samples were then flushed through the microfluidic flow cell using a syringe pump at a flow rate of ~1 µL min$^{-1}$, and a video of the fluorescent emission arising from the labeled WBCs was recorded continuously.

The imaging software defined a cascade of five (5) counters with a separation distance of ~270 µm from each other. These digital counters dynamically monitor the number of WBCs that go through the micro-channel. In order to improve the cell counting accuracy, the program counted the number of WBCs that passed through each counter line over a period of 210 frames (i.e., ~30 seconds), and this process was repeated for 5 to 6 minutes of continuous blood flow. Then the number of WBCs flowing through the chamber was estimated by averaging the counting results from these five (5) independent counters. Based on the volume flow rate and the average number of the counted WBCs within a certain time frame (i.e., 30 seconds), the WBCs density in the blood sample can be dynamically estimated during the continuous flow.

Figures 10A, 10B:
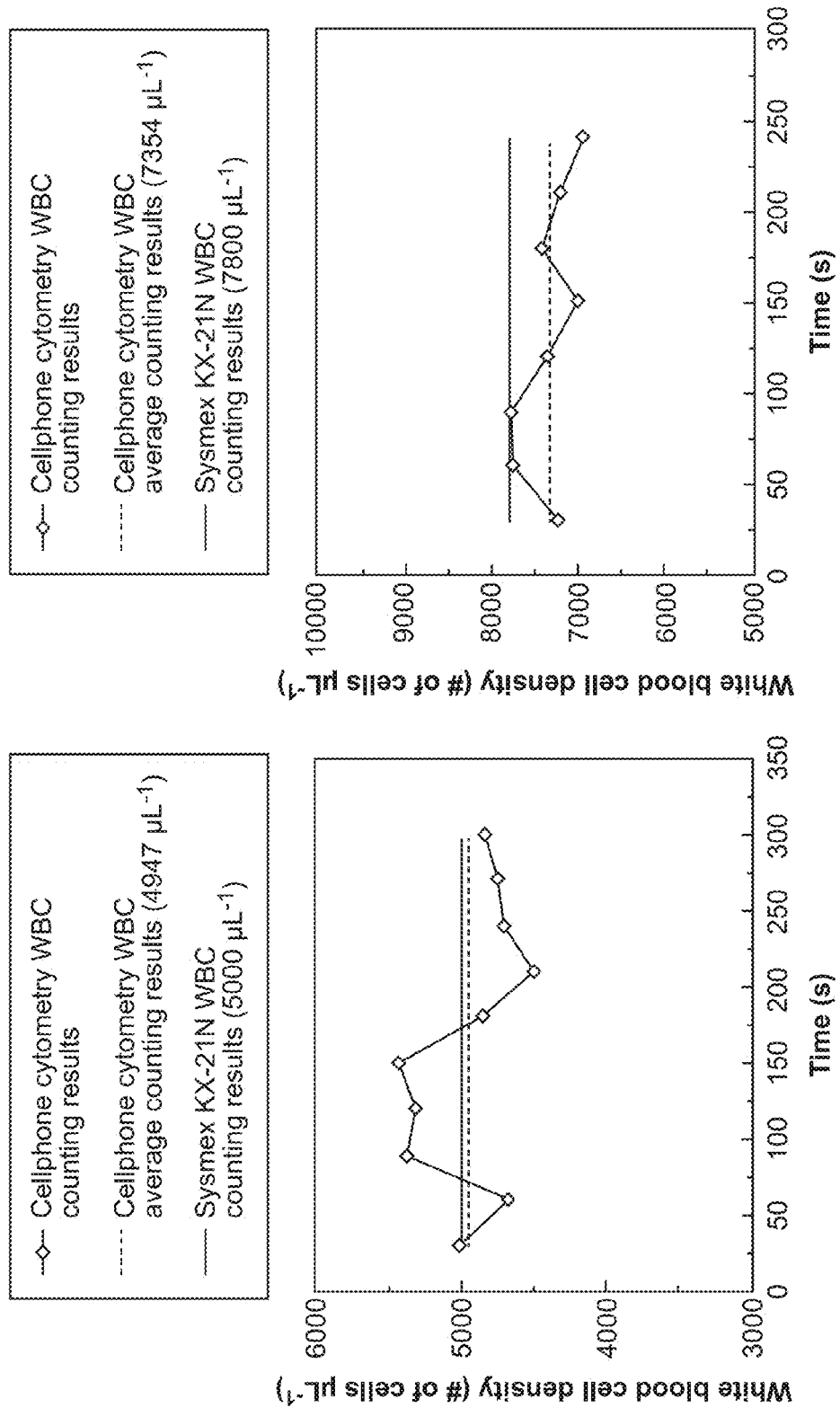
FIG. 10A illustrates automated WBC counting results obtained using the mobile phone based fluorescent imager device as well as a conventional Sysmex KX-21N device for a low density sample (5000 cells $\mu L^{-1}$).
FIG. 10B illustrates automated WBC counting results obtained using the mobile phone based fluorescent imager device as well as a conventional Sysmex KX-21N device for a higher density sample (7800 cells $\mu L^{-1}$).
Figure 11:
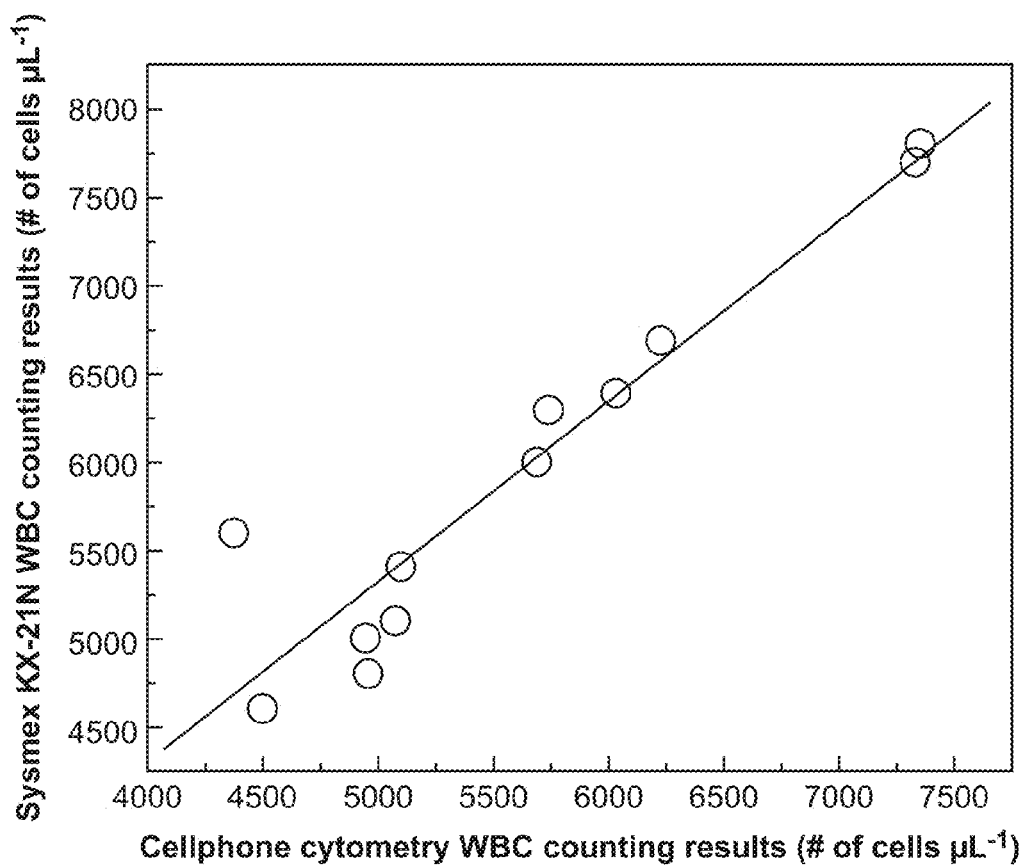
FIG. 11 illustrates a graph showing the comparison of WBC density measurement results obtained with the mobile phone based imaging flow-cytometer against the results of a commercially available hematology analyzer (Sysmex KX-21N) for 12 different patients. A linear regression of the experimental data (n=12–line) with WBC concentrations ranging from ~4000 $\mu L^{-1}$ to 8000 $\mu L^{-1}$ demonstrates a good agreement between the two modalities with a correlation coefficient of ~0.95.

FIGS. 10A and 10B illustrate two representative WBC counting curves, in which the WBC density in two different whole blood samples was plotted as a function of time. The average WBC density for each sample was also calculated by averaging each one of these curves over 5-6 minutes and the results were compared to the standard test results obtained from a commercially available hematology analyzer (Sysmex KX-21N). As shown in FIGS. 10A and 10B, the WBC density results matched well with the standard test results with <5% error. To further evaluate the mobile phone based imaging cytometry platform and its counting accuracy, twelve (12) different patients' blood samples were imaged that had varying WBC densities. Each sample was imaged for 5 to 6 minutes and average WBC density of the whole blood was estimated by processing its corresponding fluorescent video captured by the mobile phone cytometer. FIG. 11 compares the WBC densities obtained using the mobile phone imaging cytometer to the standard results obtained with Sysmex KX-21N hematology analyzer, which showed a good correlation to the mobile phone platform measurements. For the twelve (12) patients' blood samples (with WBC densities ranging from ~4000 µL$^{-1}$ to 8000 µL$^{-1}$), a correlation coefficient of ~0.95 was obtained between the two methods, demonstrating the accuracy of the optofluidic mobile phone cytometry platform.

Besides counting accuracy, throughput is also an important parameter for an imaging cytometer. The throughput in the mobile phone-based flow cytometry system is mainly determined by the mobile phone's camera frame rate. In the implementation tested herein, the camera has a relatively slow frame rate of ~7 fps. To further increase the throughput, a mobile phone camera with a higher frame rate, e.g., LG Dare VX9700, can be used which can achieve a frame rate of ~120 fps. This could potentially further improve the flow rate and thus the counting throughput by e.g., >15 fold, which would reduce the imaging time for e.g., a whole blood sample to <20 seconds per test.

Figure 13:
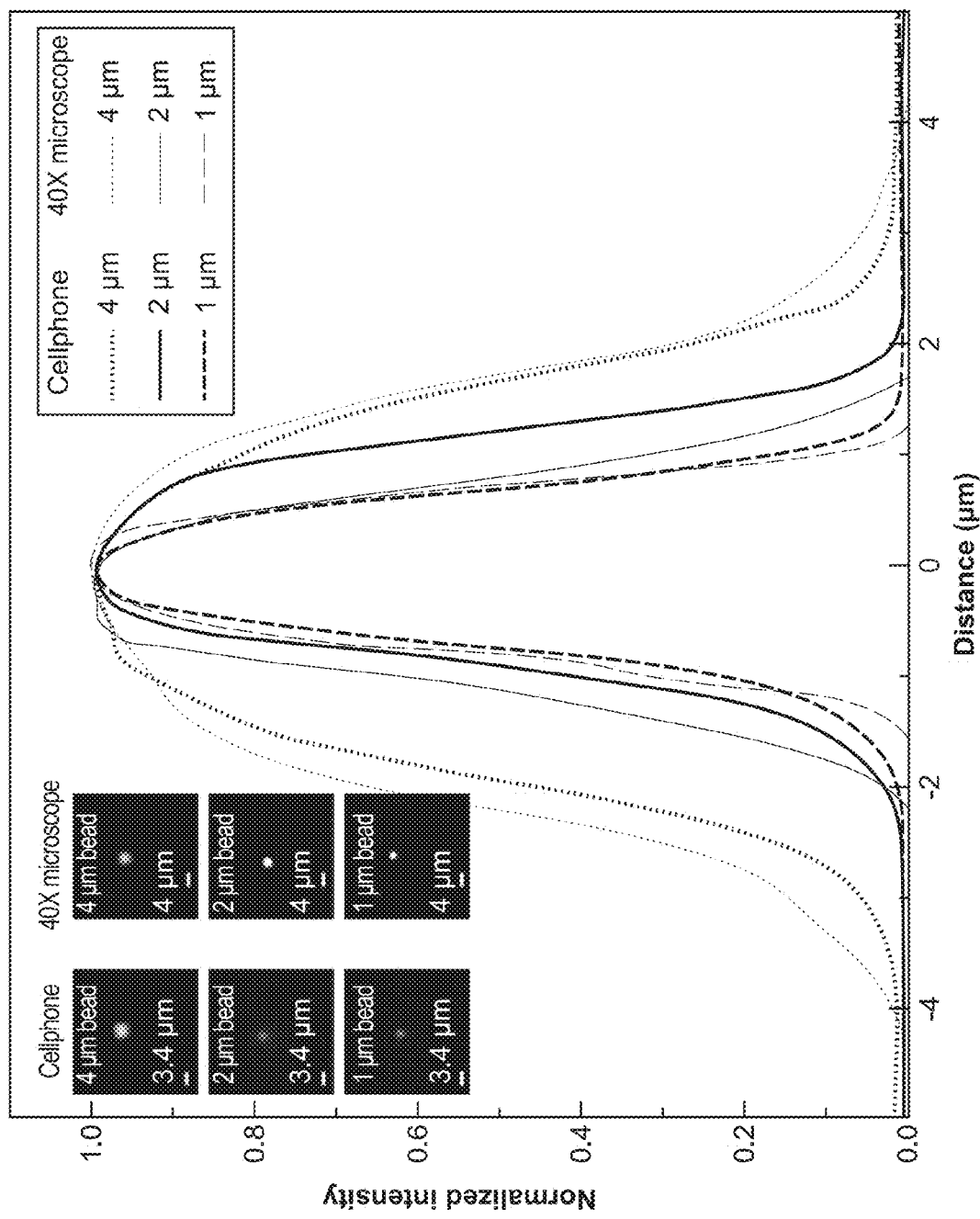
FIG. 13 illustrates the cross-sectional profiles of 4 µm, 2 µm and 1 µm fluorescent beads obtained using the mobile phone based optofluidic fluorescent microscope and a bench-top fluorescent microscope using a 40× objective-lens. These cross-sectional profiles are obtained from the inset bead images.

Finally, the spatial resolution of the optofluidic design was tested by imaging static fluorescent objects. By changing the external lens of the attachment to the mobile phone to a focal length of ~0.6 mm, a geometrical magnification of ~7.8× was achieved, such that the effective pixel size at the sample plane was <0.3 µm. The system spatial resolution was characterized using green fluorescent beads with various sizes including 4 nm, 2 nm, and 1 nm. FIG. 12A (top row) illustrates the imaging performance of the mobile phone based optofluidic fluorescent microscope for several set of beads. For comparison purposes, the same beads were also imaged by a conventional bench-top fluorescent microscope using a 40× (NA=0.6) microscope-objective as shown in FIG. 12B (bottom row). Based on images B-1 and C-1 in FIG. 12A, the mobile phone based imaging platform can easily resolve two (2) fluorescent beads that are separated by 4 µm (center-to-center). As seen in FIG. 12A (image (E-1)), two (2) beads with a center-to-center distance of 2 µm are also successfully resolved by the mobile phone fluorescent microscope. This spatial resolution level is also validated through cross-sectional profiles of isolated 1 µm fluorescent particles as illustrated in FIG. 13, which illustrates a Full-Width-Half Maximum (FWHM) of ~1.8 µm.

In this alternative embodiment, optofluidic fluorescent microscopy and flow-cytometry are integrated on a mobile phone using a compact, light-weight and cost-effective attachment to the existing camera unit of the mobile phone. In this mobile phone based optofluidic imaging cytometer, fluorescently labeled particles/cells are continuously delivered to the imaging volume through a disposable microfluidic chip that is placed above the existing camera unit of the mobile phone. The same microfluidic device also acts as a multi-layered optofluidic waveguide and efficiently guides the excitation light, which is butt-coupled from the side facets of the microfluidic channel using inexpensive LEDs. The performance of the mobile phone based imaging cytometer was tested by measuring the density of WBCs in whole blood samples, providing a good match to a commercially available hematology analyzer. The imaging performance of the platform was further tested to demonstrate a fluorescent resolution of ~2 μm. This mobile phone enabled optofluidic imaging flow cytometer could be particularly useful for rapid and sensitive imaging of bodily fluids for e.g., conducting various cell counts or for screening of water quality in resource-limited locations.

Figure 14:
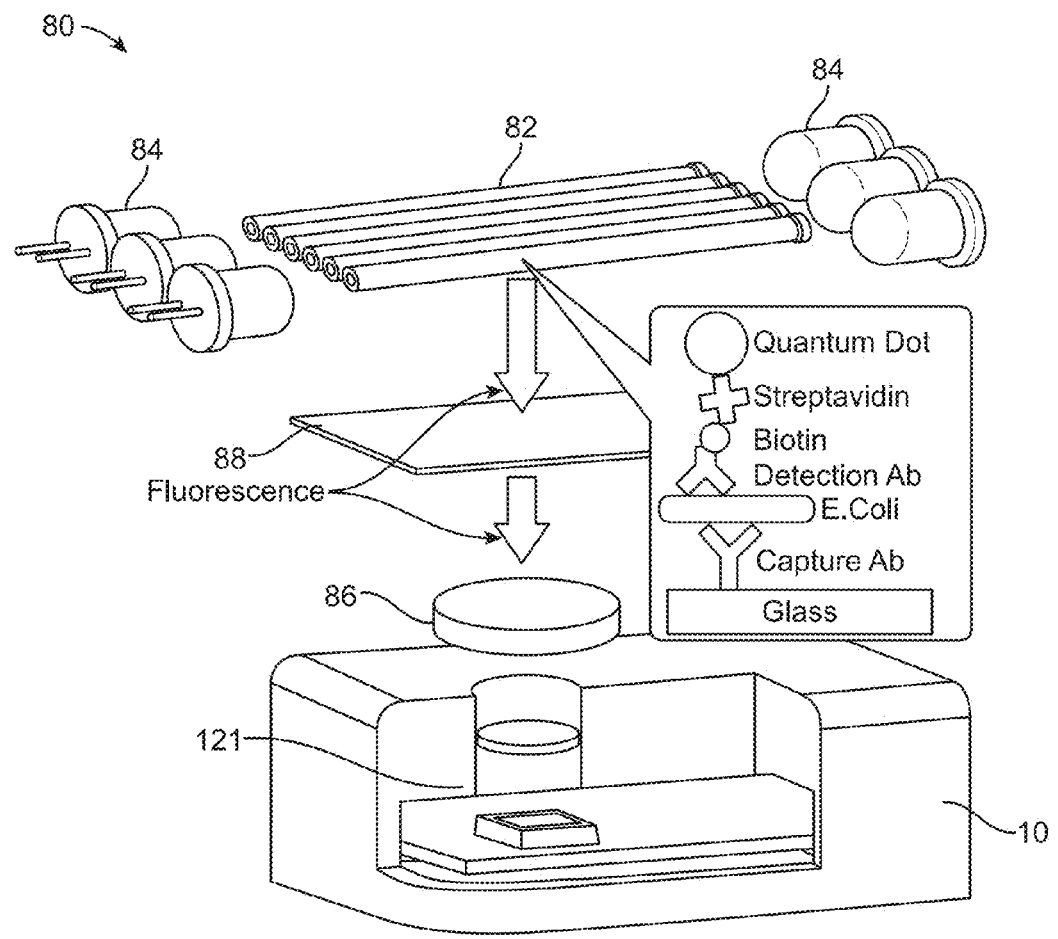
FIG. 14 illustrates an embodiment of a fluorescent imager used to detect *E. coli* particles within a sample of interest.

FIG. 14 illustrates an embodiment of a fluorescent imager 80 that utilizes an array of capillary tubes 82 (e.g., glass capillary tubes) that works as an E-coli detection platform for the screening of liquid samples. The fluorescent imager 80 works in conjunction with a mobile device 10 having a camera element 12 therein as discussed previously. The fluorescent imager 80 contains components within a housing (not shown in FIG. 14 for clarity purposes) that is modular with respect to the mobile device 10. The fluorescent imager 80 includes an excitation light source 84 which may include battery powered ultra-violet (UV) LEDs that are directly butt coupled to the capillary tubes 82. Each capillary tube of the capillary tube array 82 is filled with liquid and acts as a waveguide for the UV light and enables uniform excitation of quantum dot-labeled *E. coli* particles captured on the capillary interior surface. The capillary tubes of the array 82 serve as substrates to perform a quantum dot based sandwich assay to detect *E. coli* particles.

The emitted fluorescence light is imaged by the mobile phone camera element 12 through a lens 86 (focal length: 15 mm) that is interposed between the camera element 12 and the capillary array 82. Because the guided excitation light propagates perpendicular to the detection path, this platform permits the use of an inexpensive long pass glass filter 88 (cut-off wavelength at ~620 nm) to remove scattered UV light and create the dark-field background that is required for fluorescent imaging.

The glass capillaries of the array 82 can be functionalized with anti-*E. coli* O157:H7 antibodies using standard surface chemistry protocols to specifically capture *E. coli* O157:H7 particles in liquid samples. This functionalization process involves various steps. First, the glass capillaries are cleaned and hydrophilized with a 1:1 mixture of hydrochloric acid and methanol for ~30 minutes at room temperature and washed with DI water. The capillaries are then filled with 1% (v/v) 3-(Aminopropyl)triethoxysilane in 10% ethanol for one (1) hour and thoroughly cleaned with DI water. The aminosilanized capillaries are activated with 5 mM homofunctionilized cross-linker Bis(sulfosuccinimidyl) suberate (BS$^3$) solution in PBS buffer for ~one (1) hour. After rinsing the capillaries with PBS buffer, the capillaries were filled with 100 μg/mL anti-*E. coli* O157:H7 antibody (KPL, MD, USA) solution to immobilize the antibodies onto the capillary interior surface covalently. The inner surfaces of these capillaries were further blocked with 2% gelatine in PBS to reduce the nonspecific binding. Following these steps, the capillaries were ready to specifically capture *E. coli* O157:H7 particles in liquid samples.

The fluorescent imager 80 can then be flushed or otherwise loaded with a sample to be tested. After a washing operation, the capillaries of the array 82 are then filled with 100 μg/mL biotinylated secondary anti-*E. coli* antibodies (KPL, MD, USA) and incubated for ~1 hour. Finally, streptavidin conjugated quantum dots (emission at 625 nm) (Life Technologies, NY, USA) at a concentration of 3 nM are introduced into the capillaries to bind to the biotinylated secondary antibodies incubating for ~30 minutes, serving as the fluorescent signal. The fluorescence emission from the quantum dots that are attached to the *E. coli* particles are then imaged with the camera element 12 of the mobile device 10. The inset of FIG. 14 illustrates an internal surface of one capillary of the array 82 in which a capture antibody is bound thereto. An *E. coli* bacterium can be seen that is bound to the capture antibody. A biotinylated secondary antibody can be seen that is bound to the *E. coli* bacterium. A streptavidin conjugated quantum dot binds to the biotinylated secondary antibody which can then fluoresce in response to excitation from the excitation light source 84. Experimental tests of the device of FIG. 14 show a detection limit of ~5-10 cfu/mL.

While embodiments have been shown and described, various modifications may be made without departing from the scope of the inventive concepts disclosed herein. The invention(s), therefore, should not be limited, except to the following claims, and their equivalents.

What is claimed is:

1. A fluorescent imager comprising:
a mobile phone device having a camera element;
a housing secured to the mobile phone device via gripping elements, the housing having a size less than 100 cm$^3$;
an array of capillary tubes disposed in the housing, the array of capillary tubes containing fluorescently labeled particles;
an excitation light source disposed in the housing and butt-coupled with the array of capillary tubes to illuminate the capillary tubes with a first wavelength in a first direction and wherein the fluorescently labeled particles emit fluorescent light at a second, different wavelength;
a filter holder disposed in the housing and interposed in an optical path formed between the capillary tubes and the camera element and configured to hold filter media therein that receives fluorescent light directed substantially orthogonal to the first direction and permits transmission of the fluorescent light but prevents transmission of excitation light; and
a lens disposed in the housing, wherein the lens is positioned adjacent to the camera element of the mobile phone and within the optical path and receives fluorescent light passing through the filter when the housing is secured thereto, the lens focusing fluorescent light onto the camera element.

2. The fluorescent imager of claim 1, wherein the gripping elements comprise snap-fit flanges or clips.

3. The fluorescent imager of claim 1, wherein the filter holder is one of fixed or moveable.

4. The fluorescent imager of claim 1, further comprising a battery configured to power the excitation light source.

5. The fluorescent imager of claim 1, wherein the fluorescently labeled particle comprises a pathogen or cell.

6. The fluorescent imager of claim 5, wherein the fluorescently labeled particle comprises a bacterium.

7. The fluorescent imager of claim 6, wherein the fluorescently labeled particle comprises *E. coli*.

8. The fluorescent imager of claim 6, wherein the capillary tubes are functionalized with anti-*E. coli* O157:H7 antibodies.

9. The fluorescent imager of claim 1, wherein the fluorescently labeled particle comprises an antibody.

10. The fluorescent imager of claim 1, wherein the housing weighs less than or equal to 30 grams.

11. The fluorescent imager of claim 1, wherein the fluorescently labeled particle comprises quantum dot based antibody sandwich.

12. The fluorescent imager of claim 1, further comprising anti-bacteria antibodies covalently attached to an inner surface of the capillary tubes.

13. The fluorescent imager of claim 12, wherein the anti-bacteria antibodies comprise anti-*E. coli* antibodies.

* * * * *